United States Patent
Bacich et al.

(10) Patent No.: US 10,967,149 B2
(45) Date of Patent: *Apr. 6, 2021

(54) APPARATUS AND METHOD FOR EVERTING CATHETER FOR UTERINE ACCESS FOR BIOPSY AND CYTOLOGY

(71) Applicant: CrossBay Medical, Inc., San Diego, CA (US)

(72) Inventors: Steven R. Bacich, Half Moon Bay, CA (US); Matthew Thomas Yurek, San Diego, CA (US); Piush Vidyarthi, San Rafael, CA (US)

(73) Assignee: CrossBay Medical, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/791,768

(22) Filed: Feb. 14, 2020

(65) Prior Publication Data

US 2020/0179648 A1   Jun. 11, 2020

Related U.S. Application Data

(63) Continuation of application No. 16/377,161, filed on Apr. 6, 2019, now Pat. No. 10,576,248.

(60) Provisional application No. 62/702,321, filed on Jul. 23, 2018.

(51) Int. Cl.
| | | |
|---|---|---|
| *A61M 25/01* | (2006.01) | |
| *A61M 25/10* | (2013.01) | |
| *A61B 10/02* | (2006.01) | |
| *A61B 17/34* | (2006.01) | |
| *A61B 17/42* | (2006.01) | |

(52) U.S. Cl.
CPC ..... *A61M 25/0119* (2013.01); *A61B 10/0291* (2013.01); *A61M 25/10* (2013.01); *A61B 10/0275* (2013.01); *A61B 2010/0208* (2013.01); *A61B 2017/3435* (2013.01); *A61B 2017/4225* (2013.01); *A61M 2025/1068* (2013.01); *A61M 2210/1433* (2013.01)

(58) Field of Classification Search
CPC ....... A61M 25/0119; A61M 2210/1433; A61B 10/0291; A61B 2017/4225; A61B 10/0275

See application file for complete search history.

(56) References Cited

U.S. PATENT DOCUMENTS

| | | | | |
|---|---|---|---|---|
| 2,437,329 A | * | 3/1948 | Moore | A61B 17/320708 600/570 |
| 3,053,257 A | | 9/1962 | Birtwell | |
| 3,421,509 A | | 1/1969 | Fiore | |
| 3,825,013 A | | 7/1974 | Craven | |
| 3,911,927 A | | 10/1975 | Rich et al. | |
| 4,324,262 A | | 4/1982 | Hall | |
| 4,493,711 A | * | 1/1985 | Chin | A61M 25/104 604/271 |

(Continued)

FOREIGN PATENT DOCUMENTS

WO   WO 2020/023544   1/2020

*Primary Examiner* — Sean P Dougherty
(74) *Attorney, Agent, or Firm* — Levine Bagade Han LLP

(57) ABSTRACT

An everting balloon system is disclosed that can be used for biopsy within a body of a patient or animal. The everting balloon system can be used to access a bodily cavity or vessel for tissue specimen collection at specific bodily locations. The everting catheter system described simplifies the process of tissue biopsy.

20 Claims, 31 Drawing Sheets

(56) References Cited

U.S. PATENT DOCUMENTS

| | | | |
|---|---|---|---|
| 4,681,123 A | 7/1987 | Valtchev | |
| 4,863,440 A | 9/1989 | Chin | |
| 4,946,440 A | 8/1990 | Hall | |
| 5,074,845 A | 12/1991 | Miraki et al. | |
| 5,236,423 A * | 8/1993 | Mix | A61B 1/00151 600/115 |
| 5,265,840 A | 11/1993 | Gillespie et al. | |
| 5,346,498 A | 9/1994 | Greelis et al. | |
| 5,364,345 A | 11/1994 | Lowery et al. | |
| 5,372,247 A | 12/1994 | Nishikawa | |
| 5,374,247 A | 12/1994 | Lowery et al. | |
| 5,374,261 A | 12/1994 | Yoon | |
| 5,403,310 A | 4/1995 | Fischer | |
| 5,458,573 A | 10/1995 | Summers | |
| 5,472,419 A | 12/1995 | Bacich | |
| 5,554,159 A | 10/1996 | Fischer | |
| 5,630,797 A | 5/1997 | Diedrich et al. | |
| 5,902,286 A | 5/1999 | Reitz | |
| 5,964,223 A | 10/1999 | Baran | |
| 5,993,427 A | 11/1999 | Rolland et al. | |
| 6,039,721 A | 3/2000 | Johnson et al. | |
| 6,106,524 A | 8/2000 | Eggers et al. | |
| 6,729,334 B1 | 5/2004 | Baran | |
| 9,028,401 B1 * | 5/2015 | Bacich | A61B 17/43 600/204 |
| 9,757,264 B2 | 9/2017 | Neisz et al. | |
| 10,136,937 B1 | 11/2018 | Cosman et al. | |
| 10,245,074 B2 | 4/2019 | Bacich et al. | |
| 2001/0001811 A1 | 5/2001 | Burney et al. | |
| 2002/0049441 A1 | 4/2002 | George et al. | |
| 2002/0193705 A1 | 12/2002 | Burbank et al. | |
| 2003/0109872 A1 | 6/2003 | Muzzammel | |
| 2004/0242960 A1 | 12/2004 | Orban | |
| 2005/0015047 A1 | 1/2005 | Shah | |
| 2005/0222518 A1 | 10/2005 | Dib | |
| 2005/0240147 A1 * | 10/2005 | Makower | A61B 17/320725 604/96.01 |
| 2006/0025780 A1 | 2/2006 | James | |
| 2006/0030884 A1 | 2/2006 | Yeung et al. | |
| 2006/0036271 A1 | 2/2006 | Schomer et al. | |
| 2006/0052750 A1 * | 3/2006 | Lenker | A61M 25/0017 604/164.01 |
| 2007/0010798 A1 | 1/2007 | Stoller et al. | |
| 2007/0179380 A1 | 8/2007 | Grossman | |
| 2009/0227893 A1 * | 9/2009 | Coonahan | A61B 10/0283 600/566 |
| 2010/0030256 A1 * | 2/2010 | Dubrul | A61B 17/12022 606/200 |
| 2010/0036197 A1 * | 2/2010 | Mesallum | A61B 17/0218 600/104 |
| 2010/0160823 A1 * | 6/2010 | Parihar | A61B 10/0283 600/567 |
| 2011/0066099 A1 * | 3/2011 | Hoskins | A61F 13/26 604/14 |
| 2013/0139828 A1 | 6/2013 | Rousseau et al. | |
| 2013/0197392 A1 | 8/2013 | Ritchart et al. | |
| 2013/0253426 A1 | 9/2013 | Campbell et al. | |
| 2014/0235943 A1 | 8/2014 | Paris et al. | |
| 2015/0133779 A1 | 5/2015 | Yurek et al. | |
| 2015/0142045 A1 * | 5/2015 | Bacich | A61F 2/0027 606/193 |
| 2015/0164313 A1 * | 6/2015 | Ouyang | A61B 1/05 600/103 |
| 2015/0224280 A1 * | 8/2015 | Pinchuk | A61M 25/0017 604/544 |
| 2015/0305765 A1 | 10/2015 | Fojtik et al. | |
| 2015/0351729 A1 * | 12/2015 | Chin | A61B 1/00101 600/569 |
| 2016/0095584 A1 * | 4/2016 | Almeida | A61B 10/0275 600/567 |
| 2016/0278747 A1 * | 9/2016 | Chin | A61B 10/0291 |
| 2017/0209022 A1 | 7/2017 | Molnar | |
| 2017/0354437 A1 | 12/2017 | Bacich | |
| 2018/0028215 A1 * | 2/2018 | Cohen | A61B 17/320016 |
| 2019/0009058 A1 * | 1/2019 | Bacich | A61M 25/0119 |
| 2020/0023162 A1 * | 1/2020 | Bacich | A61M 25/10 |

* cited by examiner

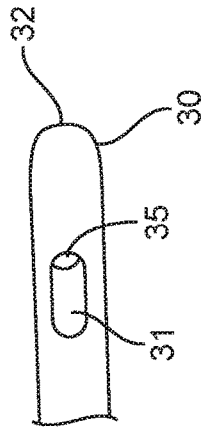
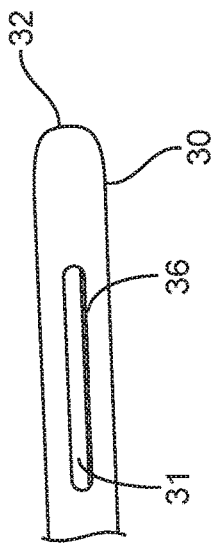
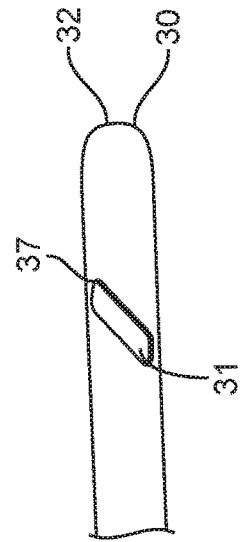
FIG. 2B  FIG. 2D  FIG. 2F
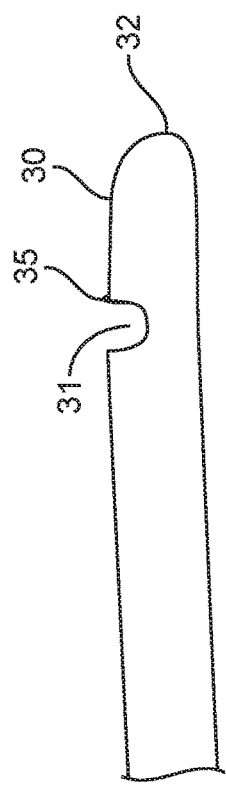
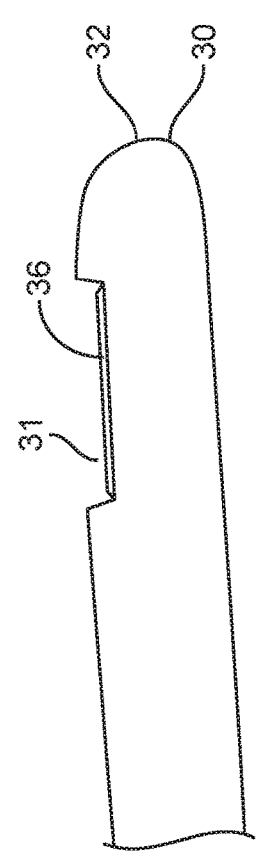
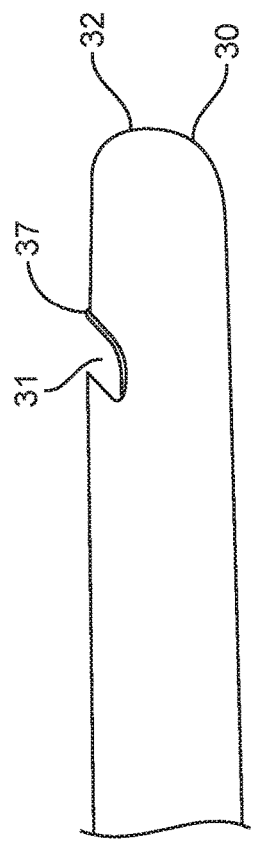
FIG. 2A  FIG. 2C  FIG. 2E

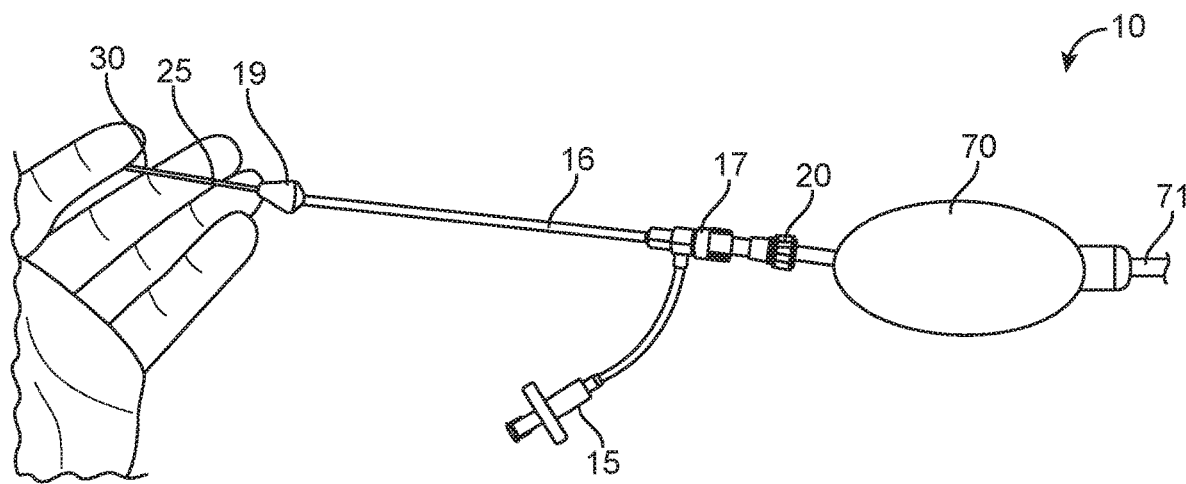
FIG. 6A
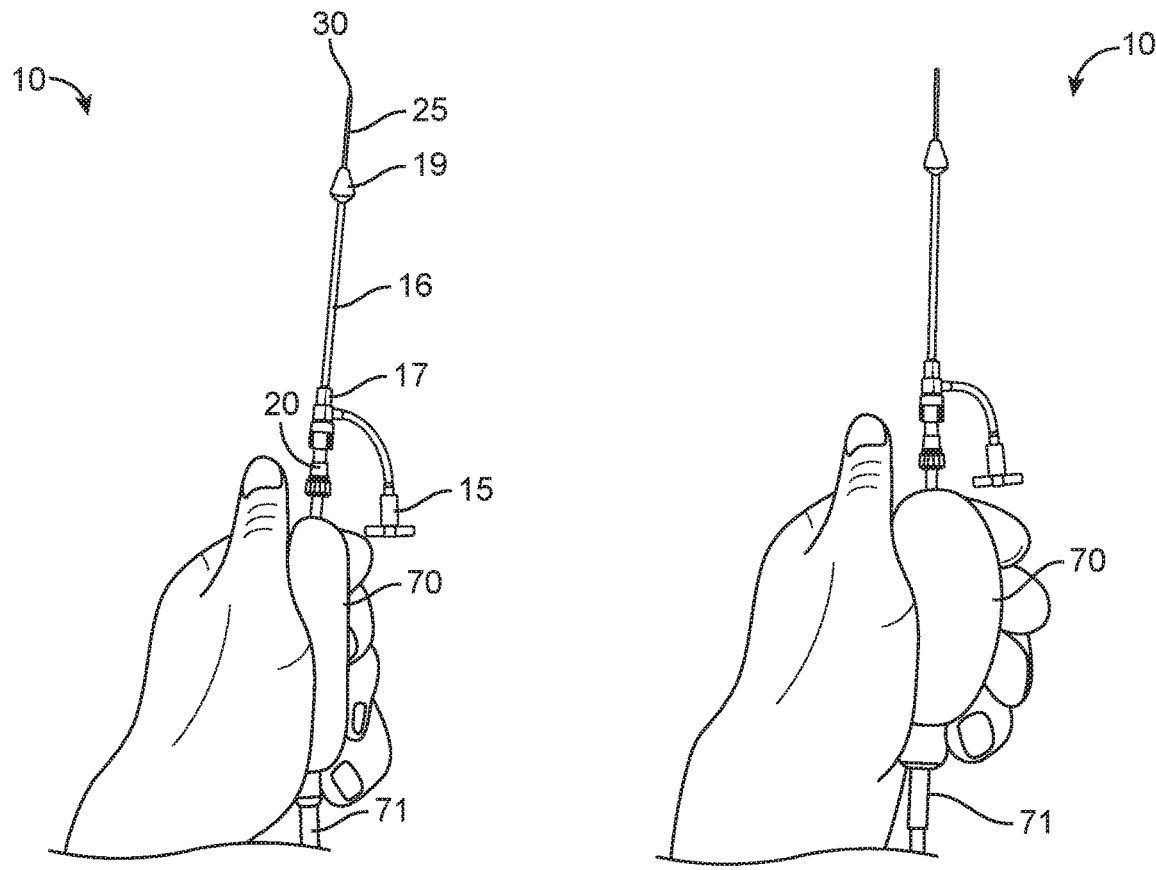
FIG. 6B
FIG. 6C

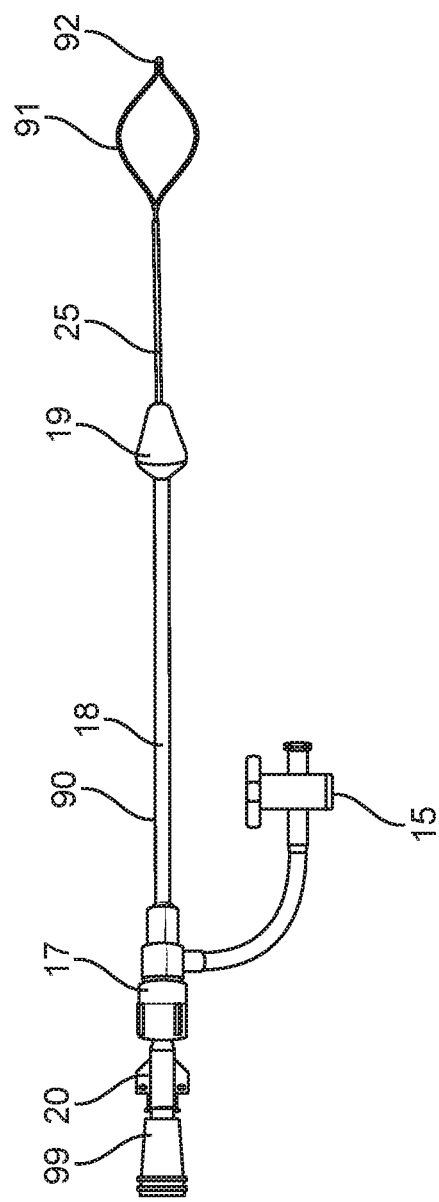
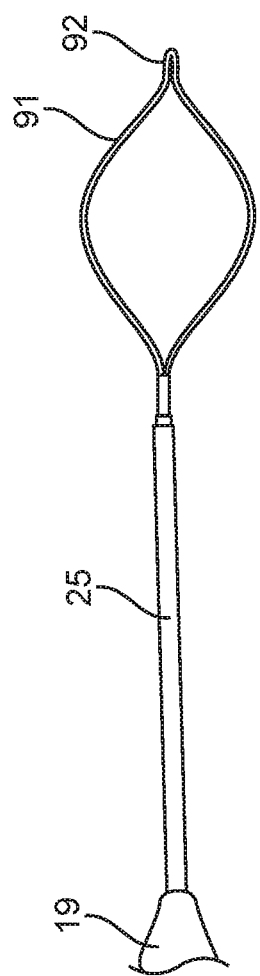
FIG. 9A
FIG. 9B

APPARATUS AND METHOD FOR EVERTING CATHETER FOR UTERINE ACCESS FOR BIOPSY AND CYTOLOGY

CROSS-REFERENCE TO RELATED APPLICATIONS

This application is a continuation of U.S. patent application Ser. No. 16/377,161, filed Apr. 6, 2019, which claims priority to U.S. Provisional Application No. 62/702,321, filed Jul. 23, 2018, which is incorporated by reference herein in its entirety.

BACKGROUND

This application has particular utility for everting catheters that are characterized with an inner catheter, outer catheter, and everting membrane that is connected to both catheters. The inner catheter may contain an inner lumen to pass fluid or media, drugs or therapeutic agents, instruments or devices such as IUD's, endoscopes, and other catheters.

For physicians and medical professionals, accessing systems for vessels and bodily cavities in patients have typically used various guidewire and catheter technologies or everting catheters. Everting catheters utilize a traversing action in which a balloon is inverted and with the influence of hydraulic pressure created by a compressible or incompressible fluid or media, rolls inside out or everts with a propulsion force through the vessel. Everting balloons have been referred to as rolling or outrolling balloons, evaginating membranes, toposcopic catheters, or linear everting catheters such as those in U.S. Pat. Nos. 5,364,345; 5,372,247; 5,458,573; 5,472,419; 5,630,797; 5,902,286; 5,993,427; 6,039,721; 3,421,509; and 3,911,927; all of which are incorporated herein by reference in their entireties. These are categorized as everting balloons and are for traversing vessels, cavities, tubes, or ducts in a frictionless manner. In other words, an everting balloon can traverse a tube without imparting any shear forces on the wall being traversed. Because of this action and lack of shear forces, resultant trauma can be reduced and the risk of perforation reduced. In addition as a result of the mechanism of travel through a vessel, material and substances in the proximal portion of the tube or vessel are not pushed or advanced forward to a more distal portion of the tube or vessel.

In addition, as the everting catheter deploys inside out, uncontaminated or untouched balloon material is placed inside the vessel wall. In the inverted or undeployed state, the balloon is housed inside the catheter body and cannot come into contact with the patient or physician. As the balloon is pressurized and everted, the balloon material rolls inside out without contacting any element outside of the vessel. Another advantage of an everting balloon catheter is that the method of access is more comfortable for the patient since the hydraulic forces "pull" the balloon membrane through the vessel or duct as opposed to a standard catheter that needs to be "pushed" into and through the vessel or duct.

Everting catheters have been described as dilatation catheters. Representative examples of dilating everting catheters include U.S. Pat. Nos. 5,364,345 and 4,863,440, both of which are incorporated by reference herein in their entireties.

Everting catheters have also been described with additional elements such as a handle for controlling instruments within an everting catheter. A representative example is U.S. Pat. No. 5,346,498 which is incorporated by reference herein in its entirety. Everting balloon catheters can be constructed with an inner catheter with an internal lumen or through-lumen (or thru-lumen). The through-lumen can be used for the passage of instruments, media, materials, therapeutic agents, endoscope, guidewires, or other instruments or devices. Representative samples of everting catheters with through-lumens are in U.S. Pat. Nos. 5,374,247 and 5,458,573. In addition, everting catheters have been described with waists or a narrowing of the balloon diameter, such as in U.S. Pat. No. 5,074,845, which is incorporated by reference herein in its entirety.

SUMMARY OF THE INVENTION

More specialized everting catheter systems have specific instruments or tools built within the catheter system. Examples of such tools or instruments are biopsy devices, cytology devices, drug delivery mechanisms, endoscopes, IUD's or other tools to be delivered into a bodily cavity, a bodily space, a potential bodily space that is created by the everting balloon mechanism, or a bodily vessel. There are several advantages to having the instrument built into the everting catheter system. The everting balloon can be used to pull the instrument into the bodily cavity without requiring the physician or operator to push the instrument into place. This is useful for tortuous or tight passageways or any pathways in which the everting balloon works to protect the body passageway from the distal end profile of the instrument while pulling the instrument into the desired location. The biopsy device is fixed to the everting catheter system and automatically extends beyond the distal end of the everting balloon by being pulled by the everting balloon into the bodily lumen, or for endometrial biopsy in the uterine cavity. During the eversion process, the biopsy device is shielded from the body tissue until it extends beyond the distal end of the everting balloon. This is particularly useful in uterine biopsy since vaginal, endocervical, or other more proximal tissue is not picked up or contaminated into biopsy device. Providing the biopsy device at a specific distance in the everting catheter system can provide the physician the ability to direct the biopsy to a specific location. Other embodiments described herein illustrate how a biopsy can be performed in a particular location in the bodily lumen or cavity. As an example, some embodiments can perform a biopsy specifically on the anterior portion of a lumen to provide the physician more directed information on the status of the patient. Other examples for locations include posterior, lateral, contralateral, multiple locations, or the progression of disease or diagnosis from the proximal portions of a bodily lumen versus more distal portions. The biopsy can be a provided by an aspiration system, cytology, tissue shaving, tissue collection, bodily fluid or materials collection, or providing a diagnostic tool within the body to indicate pH, temperature, pressure, or the presence of certain chemicals, materials, bile, blood, or other bodily materials. Once the tissue or cell biopsy is performed in the body, the everting catheter system can be removed and the everting catheter can be re-everted to retrieve the collected tissue specimen.

One embodiment of an everting catheter for performing a biopsy procedure is an aspiration mechanism or additional derivations built into the distal end of the inner catheter. The additional derivations include configurations that perform specific tissue removal processes for a desired tissue specimen type.

Additional embodiments include aspiration mechanisms that circumscribe larger areas in the bodily cavity for more wide spread tissue collection. Another embodiment includes automatic rotation of the inner catheter during the eversion and inversion step for greater area of tissue collection.

Another improvement performs the aspiration step automatically upon complete eversion.

Further improvements include mechanisms for performing aspiration in a one-handed manner or by activating the aspiration source with one button.

Another example is an everting catheter for performing biopsy is a cytology or tissue brush built within the distal end of the inner catheter. One embodiment describes a cytology or tissue brush that works with the everting balloon to trap tissue within the bristles of the brush during the inversion process.

Both of the examples of biopsy above demonstrate an everting catheter system during the inversion or retraction process that can perform biopsy at a specific location within the body without exposing the biopsy mechanism to the proximal or non-desired portion of a bodily passageway. This can be advantageous in situations where a location-specific, directed, or non-contaminated tissue specimen is desired.

Another embodiment of an everting catheter for performing biopsy is an instrument that performs tissue shaving and removal. Another embodiment for shaving and collecting tissues includes a mechanism designed to sweep a larger area for tissue collection within the desired location in the body.

Another embodiment of an everting catheter includes an everting balloon membrane surface that is designed specifically to pick up and collect tissue or cells in a location in the body. The everting membrane contains an external surface that has protruding hooks, latches, barbs, or bristles that collect tissue or cells when the everting membrane is unrolled and exposed in a specific area. Another embodiment contains a material on the exterior surface of the everting membrane with micro-channels or pores that are pressed against tissue upon eversion and pick up cellular material. Upon inversion, the tissue collection area is rolled into the everting membrane where it is contained and protected from contamination from other areas in the bodily passageway. Once the everting catheter system is removed from the body, the everting catheter can be re-everted to expose the tissue collection area for tissue specimen retrieval. In one configuration, the tissue collection area can be in the distal end of the everting membrane at the full eversion position. Other configurations can have tissue collection area of the membrane near or more proximal to the distal end of the everting membrane. Another configuration can have multiple tissue collection areas by radial segments or stripes to biopsy different locations of a bodily passageway which may facilitate the extent or proliferation of a disease state. Yet further, the tissue collection areas can be placed in anterior and posterior locations of an everting membrane to define specific locations of studied cells or tissue.

Another embodiment for specifically collecting bodily fluid within a specific location in the body has an everting membrane lined on the exterior surface with a porous or fluid receptive membrane or material for fluid collection. Upon eversion, the fluid collecting areas of the everting membrane would be in contact with a specific bodily location within the passageway or body cavity.

Another embodiment has an everting balloon membrane with a diagnosing material on the external surface. The diagnosing material can be designed to determine pH, lactate, hormonal content, medication content, urine, fecal, blood, lymphatic fluid, bile, mucus, infection or pus, edema, or other detectable bodily fluid or by-product. The diagnosing material can be placed on the external surface of the everting membrane as a test strip. Other versions of a test strip can detect and report temperature exposure, amount of pressure exerted as in pressure-sensitive test strips, or interior surface morphology of tissue within a bodily vessel.

Another embodiment can include a through-lumen within the inner catheter for irrigation or lavage of tissue to facilitate cellular or specimen collection. Adding irrigation can facilitate the collection of cells such as obtaining endometrial cells for determining endometrial receptivity for in vitro fertilization procedures.

Another embodiment can include a tissue agitator on the everting membrane to facilitate tissue or cellular collection. Another embodiment has a tissue agitator on the inner catheter of the biopsy device that performs the function of agitation automatically upon eversion or inversion. The physician or operator can manually advance or retract, or rotate, the entire everting catheter system to facilitate tissue agitation to increase the amount of tissue for specimen collection.

The device can be used for atrophic endometrium or post-menopausal women. The device can include a tissue shaver for removing and collecting thin layers of tissue within the uterine cavity.

The tissue shaver can have both external and internal collection apparatus with and without internal aspiration.

The tissue shaver can include an internal coring apparatus.

The tissue shaver can include a cellular collection and filtration system that can include an irrigation source for the uterine cavity.

A method for retrieving a tissue sample from a uterus is disclosed. The method can include inserting a distal end of an elongated element into the uterus, positioning the tissue sample in the elongated element, and closing the cover over the opening. The elongated element can have a receiving volume, such as a reservoir or a lumen of the elongated element, to receive the tissue sample. The receiving volume can have an opening and a cover closeable over the opening. The opening can have or be a port on a lateral side of the elongated element.

The method can include, after closing the cover, translating the receiving volume out of the uterus, through the cervix, and through the vagina. The cover can be kept or remain closed while the receiving volume passes out of the uterus, through the cervix, and through the vagina. The translating of the receiving volume can include translating the elongated element. The translating of the receiving volume can include translating the elongated element concurrently together with the receiving volume. The cover can have or be an everting member. The translating of the receiving volume can include inverting or everting the cover. Closing of the cover can include inverting or everting the cover (e.g., the everting member, such as a membrane) over the opening.

The method can include separating the tissue sample from tissue adjacent to the tissue sample in the uterus. The opening can have or be a port on a lateral side of the elongated element.

The method can include taking a biopsy of the uterus resulting in separating the tissue sample from the uterus. The taking of the biopsy can include the positioning of the tissue sample.

The method can include separating with a wire the tissue sample from surrounding tissue, wherein the wire is at least partially in the elongated element. The positioning of the tissue can include applying suction across the opening. The suction can pull the tissue sample into the lateral port and into the lumen of the elongated element.

A method for retrieving a tissue sample from a uterus is disclosed that can include inserting a distal end of an elongated element into the uterus. positioning the tissue sample in the elongated element, and covering the opening. The elongated element can have a closed distal terminal end and a receiving volume, such as the lumen or a reservoir, to receive the tissue sample. The receiving volume can have an opening, such as one or more lateral ports on the elongated element.

The everting member can be attached to the elongated element. The everting member can have a first retracted configuration and a second extended configuration. In the first configuration, the distal terminal end of the everting member can be proximal to the opening. In the second configuration, the distal terminal end of the everting member can be distal to the opening. The covering of the opening can include moving the everting member from the first configuration to the second configuration. The entire everting element can be radially outside of the elongated element in the first configuration and the second configuration An apparatus for separation of a tissue from a remote position is disclosed. The apparatus can have an elongated element and an everting membrane. The elongated element can have a lumen and a distal tip. The distal tip can have a first lateral port in communication with the lumen. The distal terminal end of the elongated element, such as the distal facing surface, can be closed or otherwise have no ports or fenestrations.

The everting membrane can be radially outside of the elongated element. The everting membrane can have a first proximal configuration and a second distal configuration. In the first configuration, the distal terminal end of the everting membrane can be proximal to the lateral port. In the second configuration, the everting membrane can create a fluid-tight seal, cover, obstruct or otherwise block the lateral port.

The apparatus can have a suction source in fluid communication with the lumen. The apparatus can have an irrigation source connected to the lumen. The lumen can have an irrigation channel. The irrigation source can be connected to the irrigation channel.

The apparatus can have a cutting wire extending through the lumen. The wire can have a longitudinal axis and a first protrusion at a distal end of the cutting wire. The first protrusion can extend laterally away from the longitudinal axis. The wire can have a first configuration where the first protrusion is fully inside of the lumen, and a second configuration where the first protrusion extends laterally out of the first lateral port. The cutting wire can be configured to rotate about the longitudinal axis. The cutting wire can change from the first configuration to the second configuration during the rotation about the longitudinal axis.

The apparatus can have an everting member radially outside of the elongated element.

The distal tip of the elongated element can have a second lateral port. The cutting wire can have a second protrusion. When the wire is in the first configuration, the second protrusion can be fully inside of the lumen. When the wire is in the second configuration, the second protrusion can extend laterally out of the second lateral port.

The wire can have a distal terminal tip. The distal terminal tip can be in contact with the inside surface of the lumen. Pressing the wire longitudinally can press the distal terminal tip against the inside surface of the lumen. The wire can then deform, bias, or translate (e.g., with or without deformation) into the second configuration.

The first and/or second protrusions can have V shapes.

BRIEF DESCRIPTION OF THE DRAWINGS

FIGS. 2A to 2F illustrate in both side views and top views additional derivations built into the distal end of the inner catheter.

FIGS. 6A to 6C illustrate further improvements include mechanisms for performing aspiration in a one-handed manner.

FIGS. 9A to 9D illustrate everting catheters for performing biopsy with an instrument that performs tissue shaving and removal.

DETAILED DESCRIPTION

An everting balloon system (also referred to as an everting catheter system) that can be used to traverse a vessel, such as the cervical canal for performing a biopsy procedure is disclosed. The everting balloon system can be used to access the uterine cavity via the cervix. The cervical canal is a single lumen vessel that can stretch or dilate. The everting catheter system can also traverse other locations in the body of a patient or animal for the purposes of tissue collection.

Figure 1A:
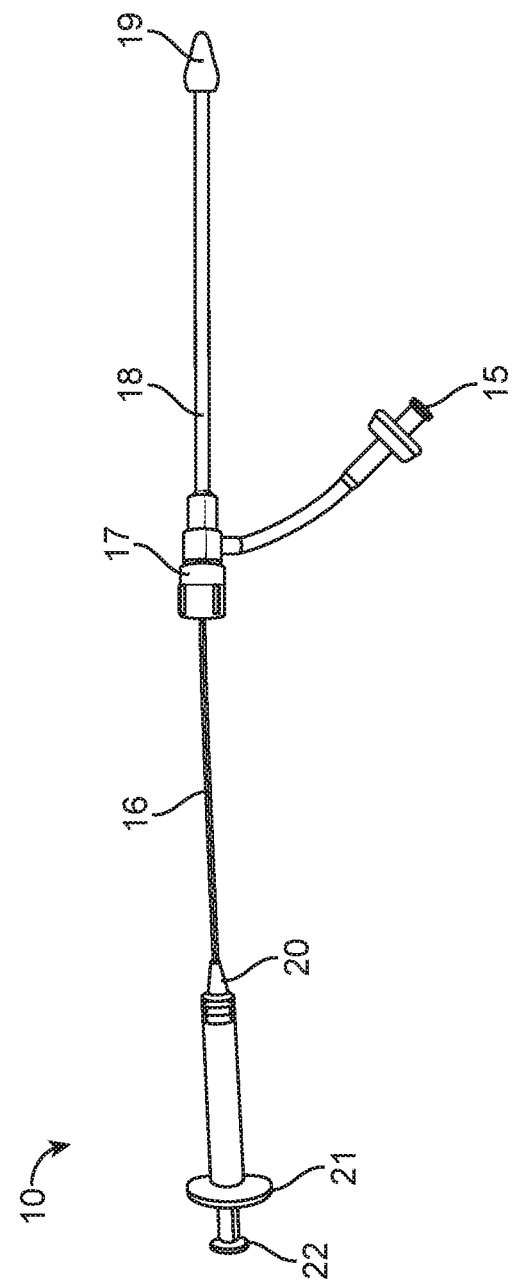
FIGS. 1A to 1F illustrate of an everting catheter for performing a biopsy procedure with an aspiration mechanism.

FIGS. 1A to 1F illustrate of an everting catheter for performing a biopsy procedure with an aspiration mechanism. FIG. 1A shows a biopsy device contained in an everting catheter system 10 in the inverted membrane position. Everting membrane and biopsy device (not visible in this figure) is contained within outer catheter 18 with acorn tip 10 at the distal end. Acorn tip 19 has an opening at the distal end (not visible). On the proximal end of outer catheter 18 there is a t-fitting or y-fitting 17 which contains an x-ring gasket (not visible). Inflation tubing and stopcock 15 supplies hydraulic energy to the everting catheter system. Hydraulic energy can be supplied by saline, air, a combination of saline and air, or gases such as $CO_2$, contrast media, culture media, and other fluids. Inner catheter 16 is translatable within the outer tubing 18 to advance and retract the everting membrane (not visible). On the proximal end of the inner catheter 16 there is a proximal hub 20 that is designed to connect to a aspiration source such as syringe 21 with syringe plunger 22. Other aspiration sources can be wall vacuum, a portable vacuum source, a syringe motor system, and other manually driven inflation devices that are driven by ratchets and screw plungers.

Figure 1B:
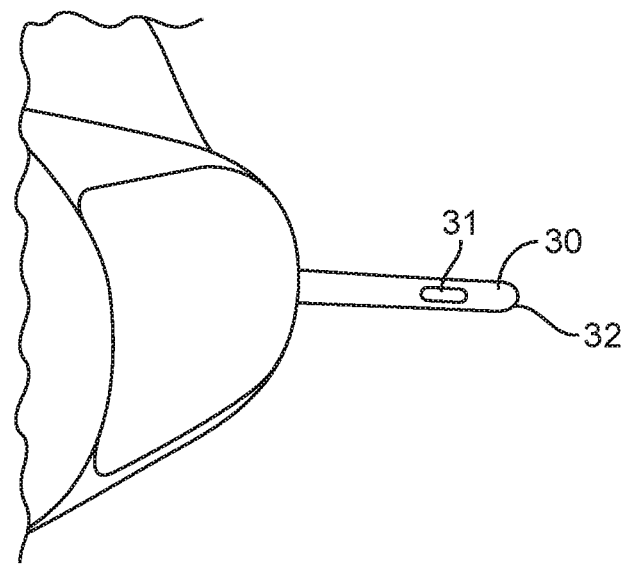

FIG. 1B shows the distal end of the biopsy device 30 in the fully everted position or when the everting membrane (not visible in this figure) is fully everted. Biopsy device 30 has rounded distal end 32 and side hole 31. Additional side holes 31 are possible including an opening at the distal end of the device, or combinations of both side holes and distal end holes. In operation when biopsy device 30 is in a body cavity such as the uterine cavity, an aspiration source can pull tissue, media, cellular material, and other bodily fluids into side hole 31. When used in conjunction with an irrigation source or lavage, side hole 31 can be used to collect both bodily materials and irrigation fluids. Side hole 31 can be used to deliver other fluids into a bodily cavity such as contrast media, echogenic fluids, and medications or therapeutic fluids.

Figure 1C:
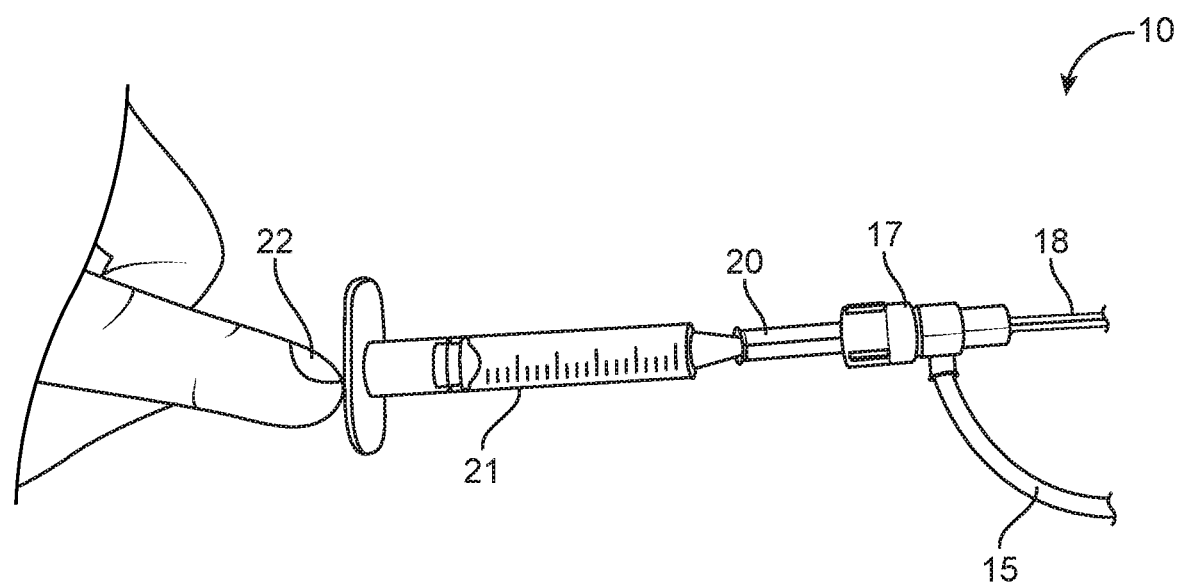

FIG. 1C shows the proximal end of the biopsy device with everting catheter 10 with outer catheter 18 attached to y-fitting 17 and inflation tubing and stopcock 15. The inner catheter (not visible) can be in the fully everted position and is contained within the outer tubing 18. Proximal hub 20 can be connected to a syringe 21 with plunger 22 in the retracted position by the user to provide negative pressure or an aspiration source.

Figure 1D:
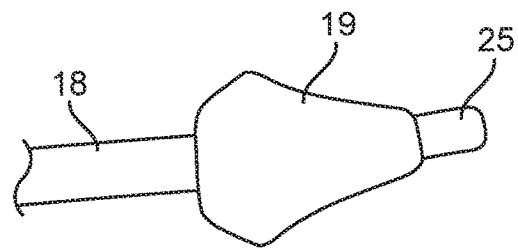

FIG. 1D shows the distal end of the outer catheter 18 and acorn tip 19 with everting membrane 25 in the initial stages of eversion advancing through the distal end opening in acorn tip 19. The everting membrane 25 can respond to hydraulic energy to roll inside out. The advancement of the everting membrane 25 can be performed by the user translating the inner catheter (not visible) or automatically in response to the hydraulic energy.

Figure 1E:
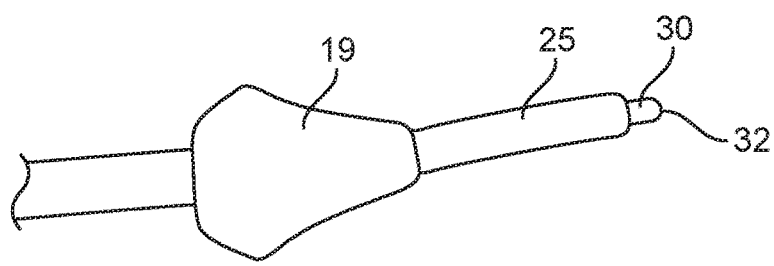

FIG. 1E shows the continuation of the eversion process with everting membrane 25 advanced further beyond the acorn tip 19. At this point in the eversion process, the distal end of the biopsy device 30 and distal rounded tip 32 can protrude from the end of the everting membrane 25. During a uterine endometrial biopsy, the everting membrane 25 can advance 1 cm to 5 cm before the biopsy device 30 protrudes from the everting membrane 25 to approximate the length of the endocervical canal. Other biopsy devices can advance a distance of 2 cm to 4 cm, or 3 cm before the biopsy device protrudes from the distal end of the everting membrane. Other biopsy devices can be made with translatable or re-positionable outer tubing (not shown) to modulate the distance the everting membrane travels in the endocervical canal prior to the biopsy device protrudes from the distal end of the everting membrane.

Figure 1F:
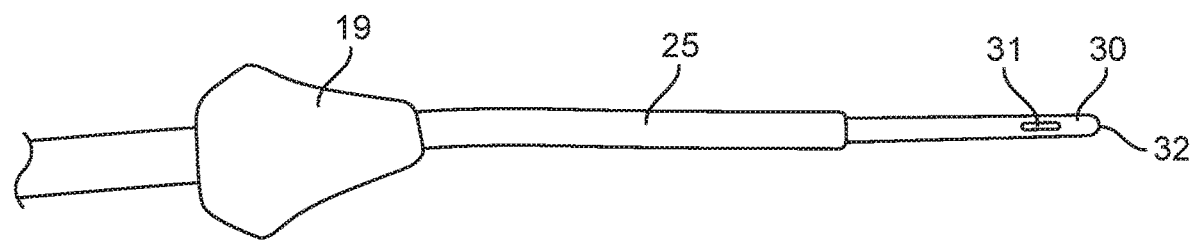

FIG. 1F shows the everting membrane 25 in the fully everted state and extending beyond the acorn tip 19. Biopsy device 30 is seen with side hole 31 and rounded distal end 32. The biopsy device is flexible and dimensioned to 1 mm to 4 mm in diameter, or 2 mm to 3 mm, and is made from Pebax, polyurethane, polypropylene, Teflon, nylon, or other biocompatible material. The everting membrane is dimensioned to be 1 mm to 5 mm in diameter for the endocervical canal, or 2 mm to 4 mm, or 3 mm, with a wall thickness of 0.001" to 0.004", or 0.0015". The everting membrane can be manufactured from irradiated polyolefin, polyurethane, Pebax, silicone, or other flexible membrane material. Side hole 31 has an elliptical opening of 0.5 mm in the minor axis and 2.5 mm in the major axis. Opening dimensions can also be circular with an opening internal diameter ranging from 0.5 mm to 4.0 mm, or 2.5 mm. In conjunction with side hole 31, negative pressure is supplied by syringe 21 as an aspiration source. With the application of negative pressure, tissue or bodily materials are collected within side hole 31 of biopsy device 30. Negative pressure is also attenuated by the pressurization of everting membrane 25 which contacts the bodily lumen or in the case of uterine biopsy, the endocervical canal to maintain an airtight seal within the uterine cavity. Also in conjunction with negative pressure, the physician can advance and retract the entire everting catheter system 10 to additionally pull tissue within side hole 31. The movements to advance and retract everting catheter system 10 while in the uterine cavity range from 0.5 cm to 2.0 cm in a back and forth manner. Everting catheter system 10 can also be rotated while in the bodily lumen or uterine cavity. During the application of negative pressure, or in conjunction with the movements on the everting catheter system 10 by the physician, tissue is drawn into biopsy device 30 and inner catheter 16. Biopsy device 30 and inner catheter 16 can be constructed from translucent or optically clear materials such as natural polypropylene, natural Pebax, Teflon, or other translucent or optically clear biocompatible materials that allow the physician to visualize the tissue being pulled into biopsy device 30.

FIGS. 2A to 2F illustrate in both side views and top views additional derivations built in the distal end of the inner catheter. FIG. 2A shows in a side view the distal end of an elongated biopsy device 30 that can have a flexible cylindrical tube with a closed and rounded distal terminal end 32 and lateral port or side hole opening 31. Additional side holes can be made on the biopsy device including an opening at the distal end of the biopsy device. Side hole opening 31 also includes an agitator member 35 that is designed to disrupt or agitate the surface of the tissue in the bodily cavity, passageway, or lumen to create more cellular matter for collection or disruption of the endometrium. In another application, it may be desirable to agitate the endometrium in a time period prior to performing an embryo transfer in vitro fertilization procedures. In operation with an aspiration source is applied to the biopsy device 30, tissue, fluids, cells, or other bodily materials are pulled into biopsy device 30.

FIG. 2B shows biopsy device 30 in a top view that illustrates the agitator member 35 at the distal end location of side hole opening 31. The agitator member 35 can be configured as a bump, barb, hook, or roughened surface and it is designed to disrupt tissue when the biopsy device 30 is advanced, retracted, or rotated about its axis. FIGS. 2A and 2B depict the agitator member at the distal end of side hole 31 but the agitator member can be on the proximal end, both ends, or have the construction of a continuous or fenestrated bump throughout the entire circumference of the side hole.

FIGS. 2C and 2D show another type of biopsy device 30 with side hole opening 31 and rounded end 32. Lateral surface of side hole opening 31 has an agitator member 36 at only one side location but both sides can contain the agitator member.

FIG. 2D illustrates in a top view further the location of agitator member 36 on the lateral side of side hole 31. In this configuration, agitator member 36 is designed to disrupt tissue as biopsy device 30 is rotated about its center axis.

FIGS. 2e and 2F illustrate another format for a side hole opening 31 that is angled to the center axis of biopsy device 30. Agitator member 37 is placed on both the lateral wall and distal end of side hole opening 31 and is designed to disrupt the tissue as biopsy device 30 is advanced, retracted, and rotated within the bodily cavity.

Figure 3A:
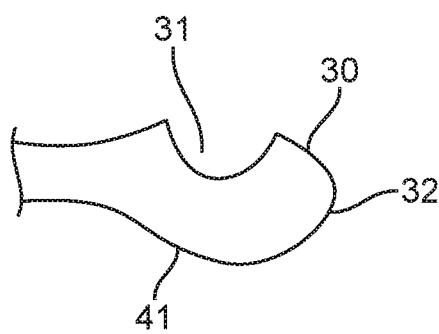
FIGS. 3A and 3F illustrate in both side views and top views aspiration mechanisms that expand or circumscribe a larger area in the bodily cavity for more wide spread tissue collection once the biopsy device exits the distal end of the everting membrane.
Figure 3B:
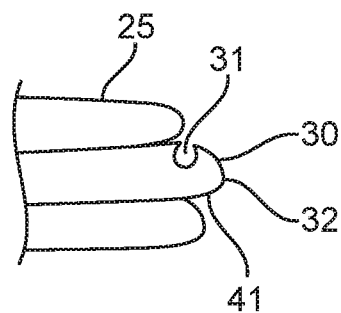
Figure 3C:
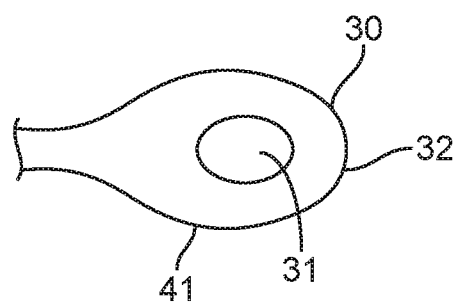
Figure 3D:
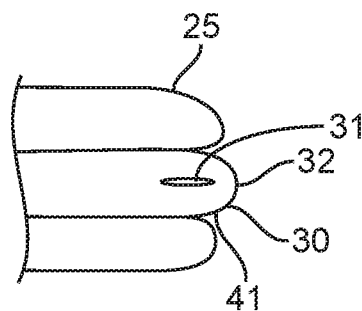
Figure 3E:
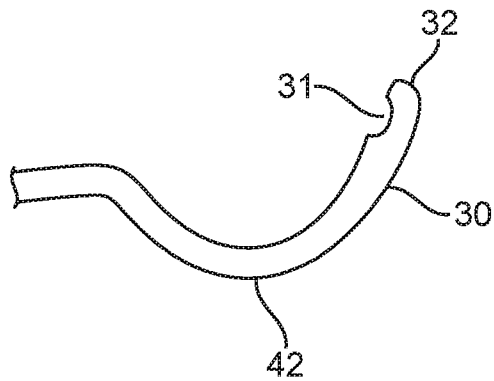
Figure 3F:
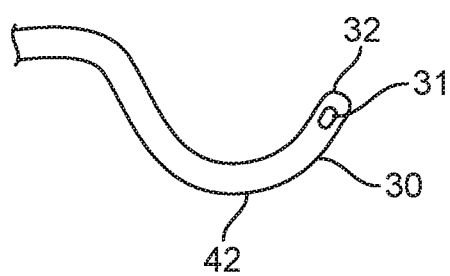

FIGS. 3A and 3F illustrate in both side views and top views aspiration mechanisms that expand or circumscribe a larger area in the bodily cavity for more wide spread tissue collection once the biopsy device exits the distal end of the everting membrane. FIG. 3A shows the distal end of biopsy device 30 after it has exited the distal end of the everting membrane. Distal end of biopsy device 30 has an expanding portion 41 that is flexible, resilient, and opens to a larger diameter after it is not contained within the everting membrane. Expansion can be achieved with resilient inner materials such as nitinol struts (not shown) that allow flexure, and a flexible material such as silicone, polyurethane, or other biocompatible flexible material that responds to the flexure provided by the nitinol struts. Struts can be constructed from other materials such as spring steel, Elgiloy, or other polymers that can act as a living hinge.

FIG. 3B illustrates the effect of everting membrane 25 on the distal end of biopsy device 30 with expanding portion 41 which is compressed to a lower profile within the everting membrane.

FIG. 3C shows in a top view expanding portion 41 of biopsy device 30, as well as the configuration of the side hole opening 31 which is fully open when the biopsy device is extended beyond the everting membrane (not visible).

FIG. 3D shows the effect of the everting membrane 25 on the configuration of the expanding portion 41 and the side hole opening 31. Note that the side hole opening 31 is now mostly closed under the influence of everting membrane 25 on the expanding portion 41 which is now compressed.

FIGS. 3E and 3F show biopsy device 30 in the fully extended position beyond the everting membrane (not shown). In the extended position, biopsy device 30 has curvature 42 near the distal end of biopsy device 30 and side hole opening 31 with rounded tip 32. In operation, curvature 42 is straightened within the everting membrane with a straight profile. Once extended beyond the everting membrane, curvature 42 circumscribes a larger area as biopsy device 30 is advanced, retracted, or rotated within the body. Curvature 42 can be created by shape memory material as an inner support material or mandrel (not shown) such as nitinol, or forming curvature 42 within the polymer material of biopsy device 30 by thermal forming or molding.

FIG. 3F shows biopsy device 30 with curvature 42 in a top view to illustrate that the curvature can be multiple in configuration and represent three-dimensional curves in x, y, and z axis.

Figure 4:
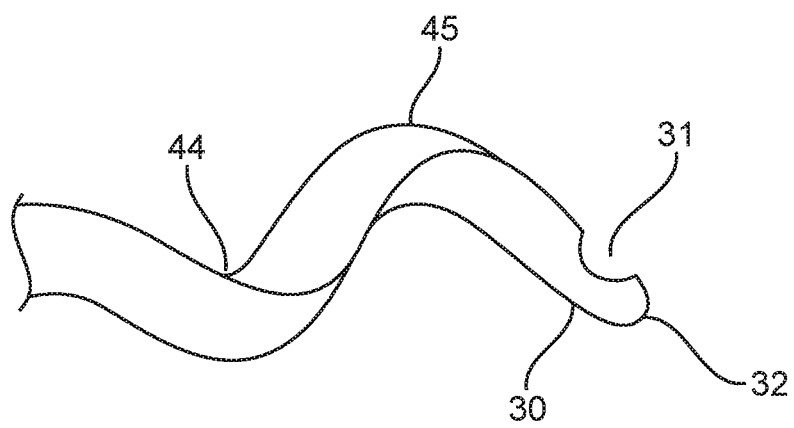
FIG. 4 illustrates an automatic rotation of the inner catheter during the eversion and inversion step for greater area of tissue collection.

FIG. 4 illustrates in a top view an automatic rotation of the inner catheter during the eversion and inversion step for greater area of tissue collection. Biopsy device 30 is fully extended from the everting membrane (not shown) and is configured like a cork screw so that side hole 31 rotates about the center axis of the biopsy device 30 as it is advance and retracted to provide greater area of tissue collection within the body.

Figure 5A:
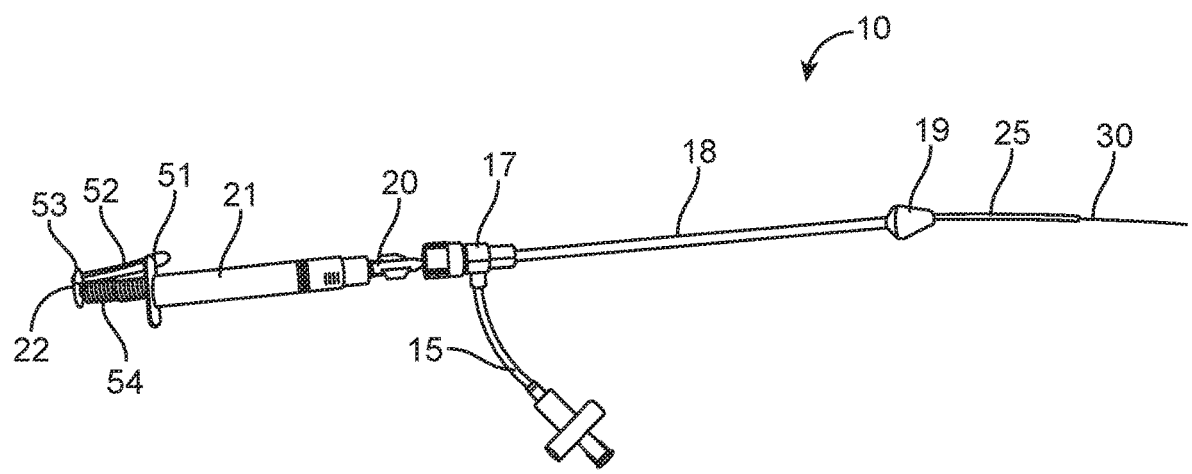
FIGS. 5A to 5C illustrate another improvement that performs the aspiration step automatically following eversion.
Figure 5B:
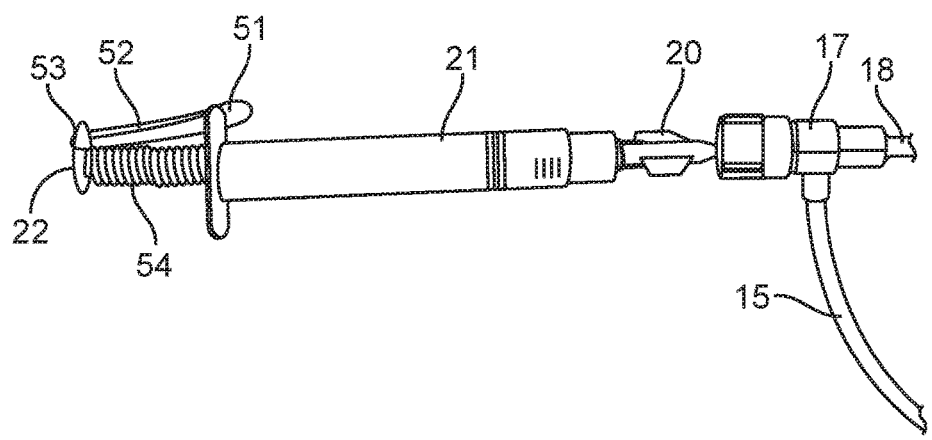
Figure 5C:
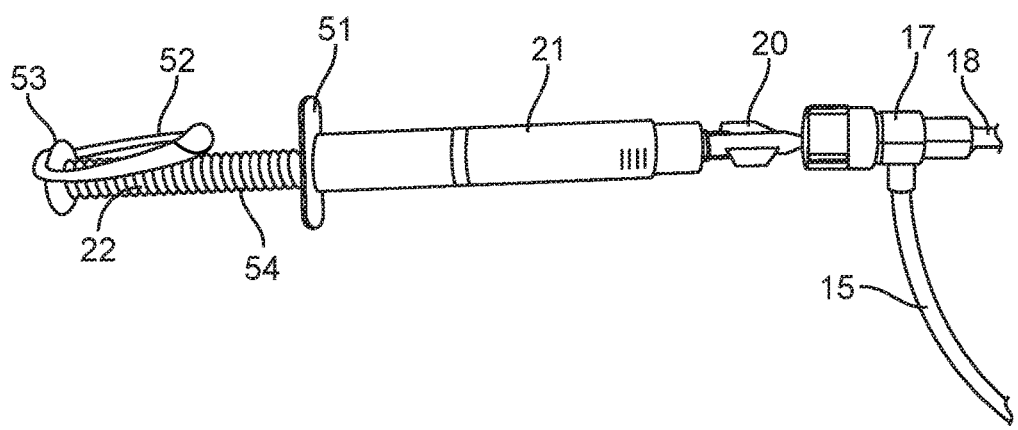

FIGS. 5A to 5C illustrate another improvement that performs the aspiration step automatically following eversion. FIG. 5A shows a biopsy device with everting catheter 10 with biopsy device 30 extending beyond the everting membrane 25 in the fully everted position with inner catheter (not visible) contained within outer catheter 18. Proximal hub 20 is adjacent to y-fitting 17 with inflation tubing and stopcock 15. Connected to proximal hub 20 is syringe 21 with syringe plunger 22 and spring 54 in the compressed condition between flange 51 and proximal portion of syringe plunger 22. Clip 52 keeps spring in the compressed condition by being constrained in flange 51 and connector 53.

FIG. 5B shows a close view of syringe 21 with compressed spring 54 and clip 52 being held by flange 52. Spring 52 can be made from stainless steel, spring steel, or polymers. Clip 52 can be made from a polymer or metal and can be configured as a latch, leash, or flap that mechanically keeps spring 54 compressed.

FIG. 5C shows spring 54 now extended with clip 52 detached from flange 51. Upon detachment, spring 52 acts on syringe plunger 22 to provide an aspiration source with syringe 21 within the biopsy device. By moving, flipping, displacing, or manipulating clip 51 off flange 51 or mechanical detent on flange 51, the physician or user can automatically provide an aspiration source without requiring the use of two hands by displacing clip 51 from flange 51 since syringe plunger 22 will withdraw and pull back from syringe 21 under the influence of the spring action or force of spring 54 to provide an aspiration source. Other embodiments can include clip 52 being restrained on flange 51 by slide button, hook, notch, or depressible button or detent (all not shown). In operation, these embodiments for displacing clip 52 provide a one-handed operation for automatically supplying an aspiration source with negative pressure of withdrawing syringe plunger 22 by the spring action or force of spring 52.

FIGS. 6A to 6C illustrate further improvements include mechanisms for performing aspiration in a one-handed manner. FIG. 6A shows another biopsy device with everting catheter 10 in the fully everted position with biopsy device 30 extending beyond the everting membrane 25. Aspiration bulb 70 with air check valve 71 is attached to the proximal hub 20.

FIG. 6B shows the user squeezing the aspiration bulb 70 which expels the air from the aspiration bulb through air check valve 71.

FIG. 6C shows the user releasing the compression on aspiration bulb 70 which creates an aspiration source through the biopsy device with everting catheter 10. Repeated squeezes or compressions, and subsequent releases on aspiration bulb 70 continue to draw aspiration pressure within the system. Other embodiments for supplying one-handed aspiration sources include mechanical flywheels, ratchet controlled pumps, or battery-operated pumps.

Figure 7A:
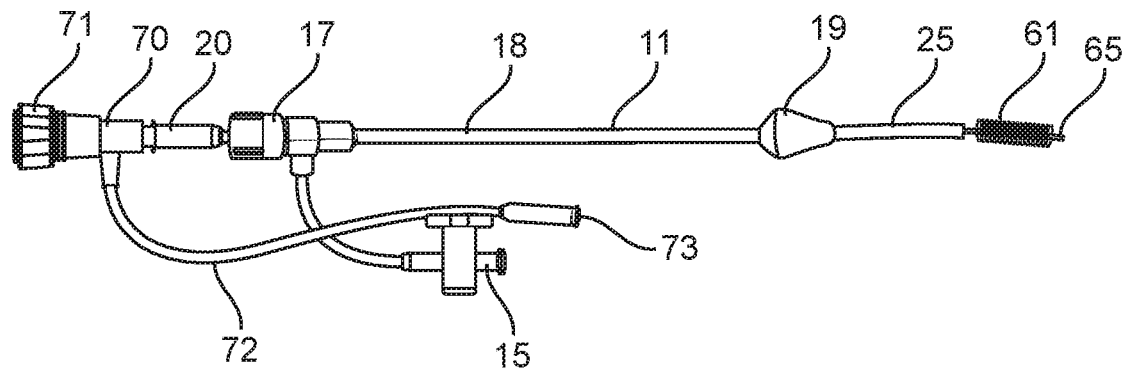
FIGS. 7A and 7B illustrate other examples of an everting catheter for performing biopsy that contains a cytology brush built within the distal end of the inner catheter.
Figure 7B:
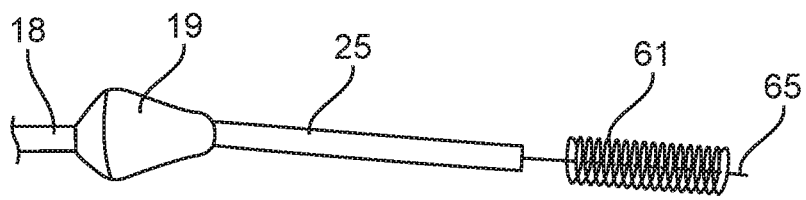
Figure 7B:
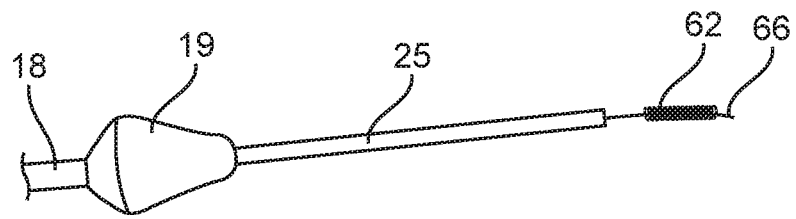

FIGS. 7A and 7B illustrate other examples of an everting catheter for performing biopsy that contains a cytology brush built within the distal end of the inner catheter. FIG. 7A shows a cytology brush within an everting catheter 11 with everting membrane 25. Cytology brush 61 has a rounded distal end 65 with brushes, bristles, absorbent materials, hooks, barbs, or other projections designed for collecting tissue, cells, fluids, or other bodily materials. Cytology brush with everting catheter 11 has a knob 71 for rotating, advancing, or retracting the distal end of cytology brush 61. T-fitting 70 has irrigation tubing 72 for supplying fluids, media, gas, or other materials through connector hub 73 through the device and out the everting membrane 25. Y-fitting with stopcock 15 is for providing hydraulic pressure to the everting catheter system.

FIG. 7B shows two different configurations of cytology brushes 61 and 62. Sizes of cytology brushes can be 1 mm to 5 mm in outer diameter, and 0.5 cm to 3 cm in length for applications in the uterine cavity. Other sizes are possible for other locations in the body. Cytology brush can be configured in the straight condition, be malleable to take a curve (not shown), have a pre-set curvature (not shown), or shaped as a loop or noose (not shown).

Figure 8A:
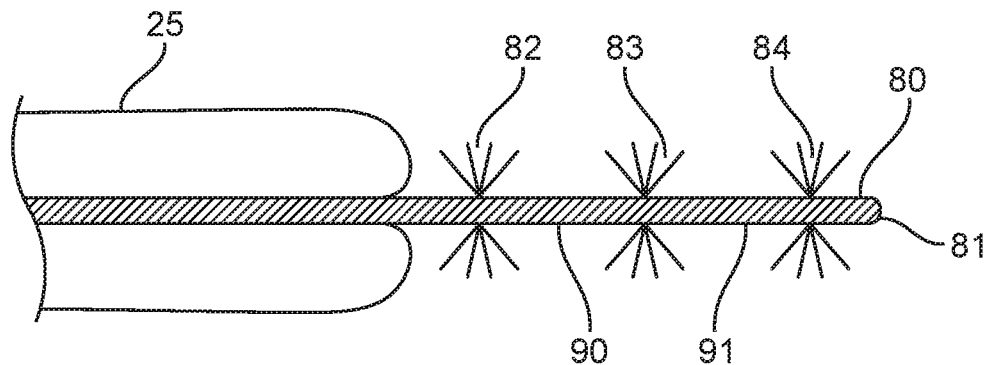
FIGS. 8A to 8D illustrate everting catheters for performing biopsy that contain a cytology brush built within the distal end of the inner catheter whereby the cytology brush works with the everting balloon as a system to trap tissue within the bristles of the brush during the inversion process.

FIGS. 8A to 8D illustrate everting catheters for performing biopsy that contain a cytology brush built within the distal end of the inner catheter whereby the cytology brush works with the everting balloon as a system to trap tissue within the bristles of the brush during the inversion process. FIG. 8A shows cytology brush 80 with distal end 81 with segmented bristles 82, 83, and 84 with bare locations 90 and 91. Cytology brush 80 is fully extended beyond everting membrane 25. In operation in a bodily cavity or location, the full extension of cytology brush 80 allows for tissue contact of the segmented brushes 82, 83, and 84. Please note that the number of segmented brushes can be 2 to a number that can fit on the cytology brush. For the uterine cavity application, 3 to 6 segmented brush locations in which each location was 3-4 mm in length with a diameter of 2 to 4 mm.

Figure 8B:
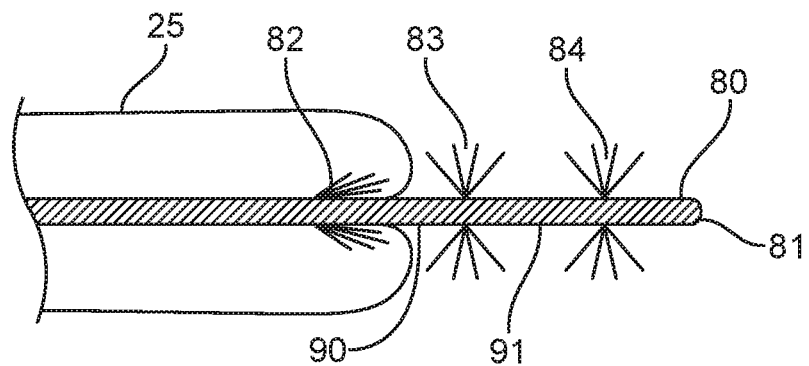

FIG. 8B shows cytology brush 80 being retracted within everting membrane 25 in which proximal segmented brush location 82 is flattened under the influence of the everting membrane. As segmented brush location 82 is flattened, bare location 90 becomes a collection point for tissue, cells, fluid, and other bodily materials. Subsequently as cytology brush 80 continues to be retracted within everting membrane 25, segmented brush location 83 will flatten and trap tissue and bodily materials in bare location 91.

Figure 8C:
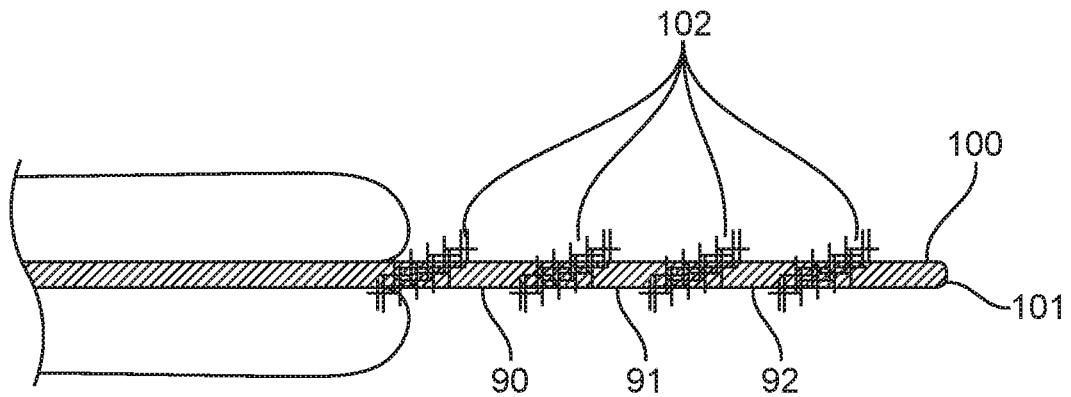

FIG. 8C shows an alternative configuration of a cytology brush 100 with segmented brushes that are in a helical configuration with continuous helix brush 102 and bare locations 90, 91, and 92. Bare locations are in fact continuous but are labeled individually for clarity.

Figure 8D:
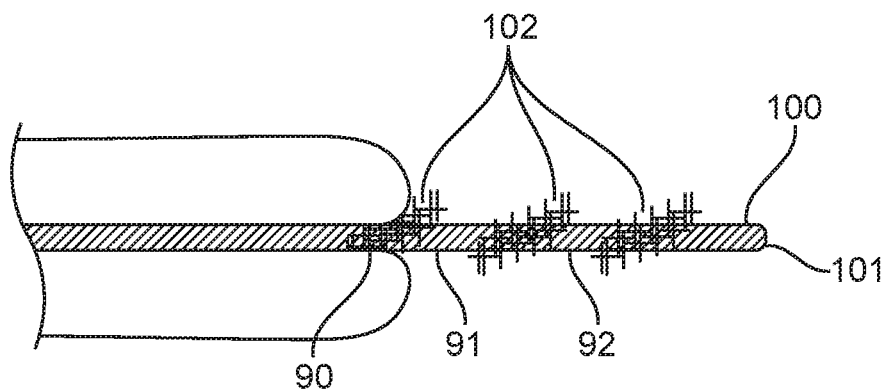

FIG. 8D shows cytology brush being retracted within everting membrane 25 in which the proximal portion of helix brush 102 is being compressed or flattened and tissue or bodily materials being collected in bare location 90.

FIGS. 9A to 9D illustrate everting catheters for performing biopsy with an instrument that performs tissue shaving and removal. Tissue shaver with everting catheter 90 is shown with open shaver 91 with shaver distal end 92. Shaver 91 is open when extended from the everting membrane 25 and shaver 91 is closed or in a low profile condition (not shown) when shaver 91 is retracted within the everting membrane 25. Proximal knob 99 allows for advancement, retraction, or rotation of shaver 91. Shaver 91 can be made from metal, nitinol, or a polymer.

FIG. 9B shows a close up view of shaver 91 and shaver end 92 extending beyond the distal end of everting membrane 25 with acorn tip 19. Shaver 91 can also be constructed with a composite of materials on the shaver 91 with a silicone, polyurethane, or other coating on the shaver 91. Coating is constructed with a roughened surface (not shown) or contains projections (not shown) to collect or trap tissue within the opening of the shaver 91. In another embodiment, the coating can be placed on the distal portion or distal half of the shaver (not shown) to trap tissue upon the closure and retraction of the shaver.

Figure 9C:
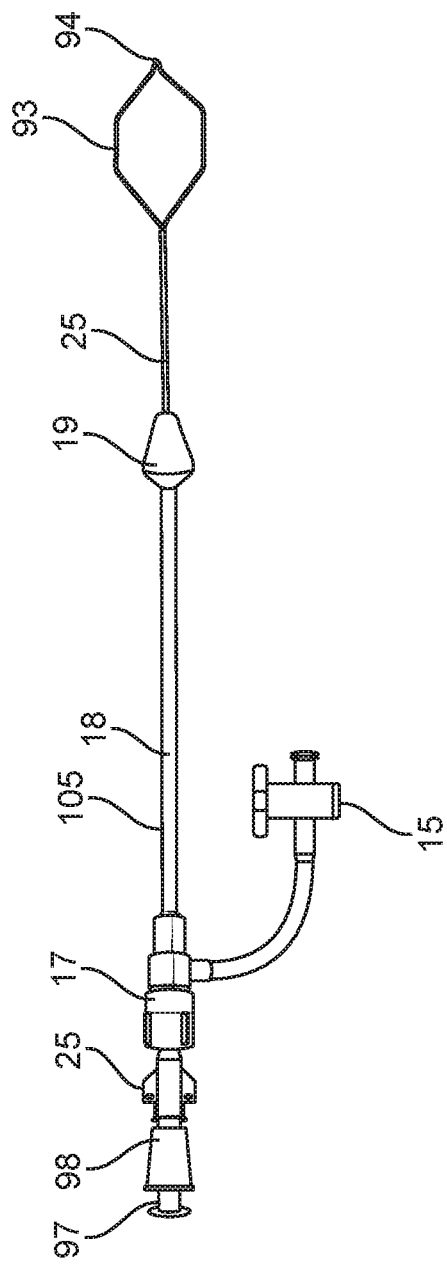

FIG. 9C shows another shaver with everting catheter 105 that opens and deploys into a larger area within the body with shaver 93 with distal end 94. The shaver 93 is in the open position after exiting the everting membrane 15 is fully everted and beyond the acorn tip 19. Everting catheter is fully everted when the inner catheter (not visible) is translated within the outer catheter 18 through the y-fitting 17 under the influence of the hydraulic pressure applied through inflation tubing and stopcock 15. Connected to proximal hub 25 is know 98 that can be used to advance, retract, and rotate shaver 93 at the distal end of the shaver with everting catheter 105. On the proximal end of knob 98 is a luer connection 97 with through hole for connecting with a syringe (not shown) for injecting irrigation fluid, contrast media, saline, gas, air, or therapeutic agents during the procedure. Luer connection 97 can also be used to supply an aspiration source (not shown) for assisting in maintaining cells, fluids, or other bodily material during the tissue shaving and collection procedure, or when retracting the device from the body.

Figure 9D:
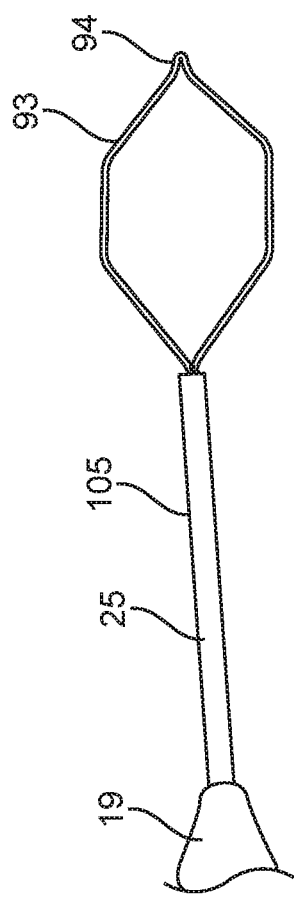

FIG. 9D is a close up view of shaver 93 with distal end 94 extending beyond the distal end of the everting membrane 25. Shaver 93 is made from stainless steel but other materials such as nitinol, Elgiloy, or polymeric materials such as polypropylene, polycarbonate, ABS, nylon, PEEK, or other biocompatible materials are possible.

Figure 10A:
FIGS. 10A and 10B illustrate an everting catheter for performing biopsy with an instrument that performs tissue shaving and removal and a mechanism designed to sweep a larger area for tissue collection within the desired location in the body.
Figure 10B:
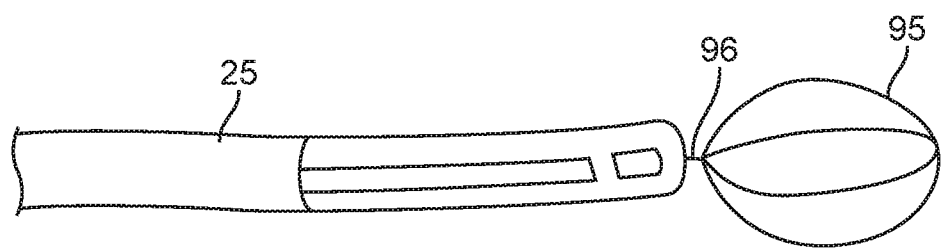

FIGS. 10A and 10B illustrate an everting catheter for performing biopsy with an instrument that performs tissue shaving and removal and a mechanism designed to sweep a larger area for tissue collection within the desired location in the body. FIG. 10A shows the distal end of everting membrane 25 with shaver 96 with distal end 95.

FIG. 10B shows shaver 96 opened and deployed beyond everting membrane 25 with shaving elements 95 constructed to remove tissue within the body. Shaver 96 can be advanced, retracted, and rotated by the physician or user. Upon retraction back into everting membrane 25, shaver 96 collapses and returns to a small profile.

Figure 11A:
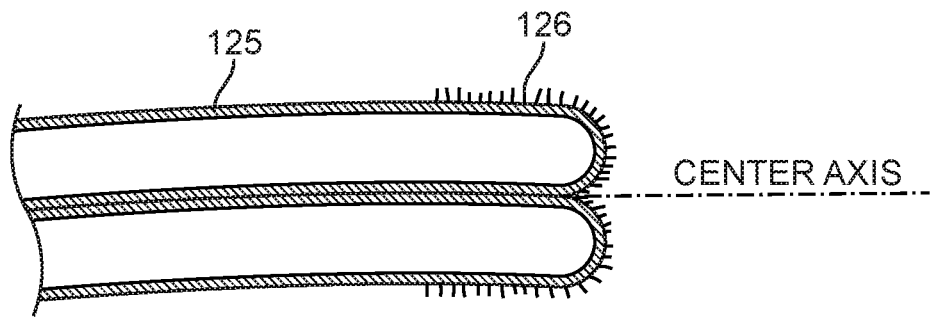
FIGS. 11A to 11D illustrate in cross-sectional views an everting catheter with an everting balloon membrane surface with protruding hooks, latches, barbs, or bristles to pick up and collect tissue or cells in a location in the body.

FIGS. 11A to 11D illustrate in cross-sectional views an everting catheter with an everting balloon membrane surface with protruding hooks, latches, barbs, or bristles to pick up and collect tissue or cells in a location in the body. In this embodiment, the everting membrane itself becomes the testing or tissue collection instrument by the physical contact of the everting membrane with the bodily cavity, passageway, lumen, or potential space. FIG. 11A shows in a cross-sectional view an everting membrane 125 that is fully everted from the everting catheter (not shown). Distal end of everting membrane 125 contains bristles 126 or a brush on the surface of the membrane. As the membrane everts and rolls out on the tissue surface, bristles 126 pick-up or collect tissue, cellular or bodily materials. As everting membrane 126 is retracts and inverts along the center axis of the everting catheter system, bristles 126 roll into the everting membrane 125 and cellular materials are collected. Note that by definition, the tissue collection or tissue sampling area is limited to only that area the everting membrane 125 and tissue collecting elements or bristles 126 contact.

Figure 11B:
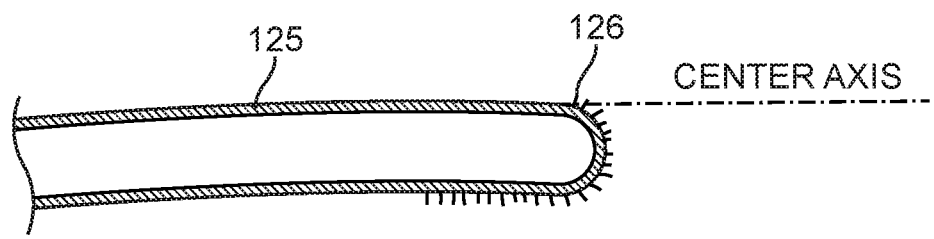

FIG. 11B shows a close up cross-sectional view of just side of everting membrane 125 and bristles 126.

Figure 11C:
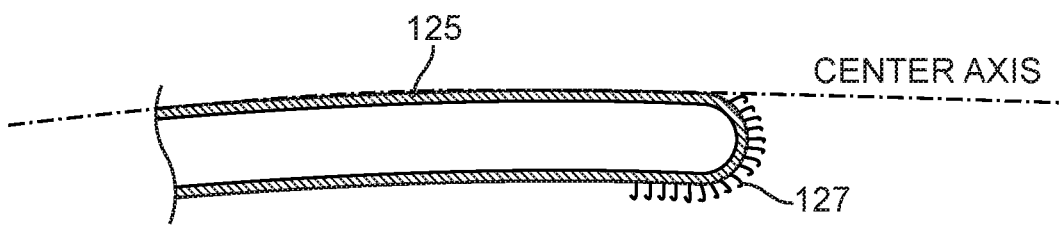

FIG. 11C shows in a cross-sectional view one side of everting membrane 125 with another embodiment of a tissue or cellular collection system made of hooks 127 or barbs. Once deployed, hooks 127 contact and collect tissue that will be trapped within the everting membrane 125 as the inversion process is done.

Figure 11D:
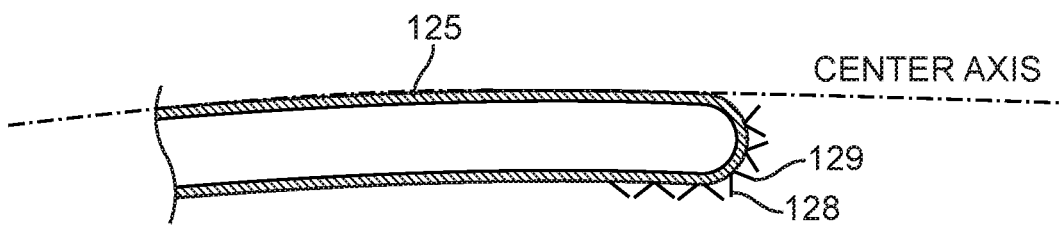

FIG. 11D shows in a cross-sectional view on side of everting membrane 125 with an alternative form of tissue collecting elements constructed with latches 128 and 129 that open and close upon physical contact with the tissue. Upon inversion, latches 128 and 129 close and trap tissue or cellular materials.

Figure 12:
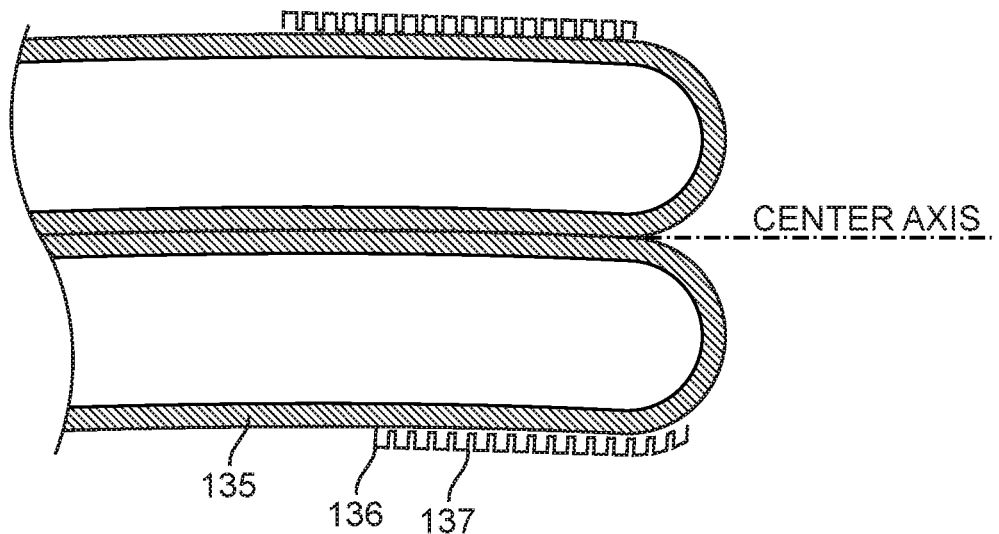
FIG. 12 illustrates in a cross-sectional view an everting balloon catheter with a material on the exterior surface of the distal end of the everting membrane with micro-channels or pores that are pressed against tissue upon eversion to pick up cellular material.

FIG. 12 illustrates in a cross-sectional view an everting balloon catheter (not shown) with cellular collection material 136 on the exterior surface of the distal end of everting membrane 135 with micro-channels 137 or pores that are pressed against tissue upon eversion to pick up cellular material. In operation, everting membrane 135 unrolls within a bodily cavity until the portion with the cellular collection material 136 contacts tissue. Upon pressure being applied with everting membrane 135, micro-channels 137 open and collect bodily materials. Upon inversion, micro-channels 137 and cellular collection material 136 portion of the device is retracted within everting membrane 135.

Figure 13:
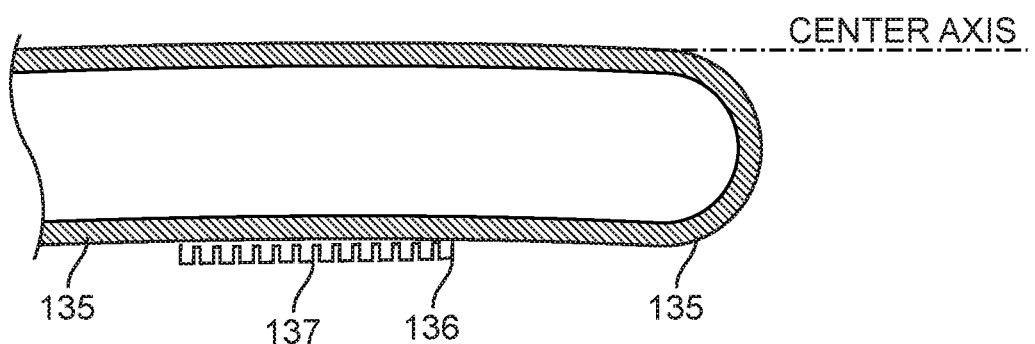
FIG. 13 illustrates in a cross-sectional view an everting balloon catheter with a material on the exterior surface that is near or more proximal the distal end of the everting membrane with micro-channels or pores that are pressed against tissue upon eversion to pick up cellular material.

FIG. 13 illustrates in a cross-sectional view an everting balloon catheter (not shown) with a cellular collection material 136 on the exterior surface that is near or more proximal the distal end of the everting membrane 1315 with micro-channels 137 or pores that are pressed against tissue upon eversion to pick up cellular material. This embodiment demonstrates that the cellular collection material 136 can be placed on specific locations on the everting membrane 135 that are not on the distal end of the membrane or a particular side of the everting membrane including the anterior, posterior, lateral, or combinations of these locations.

Figure 14:
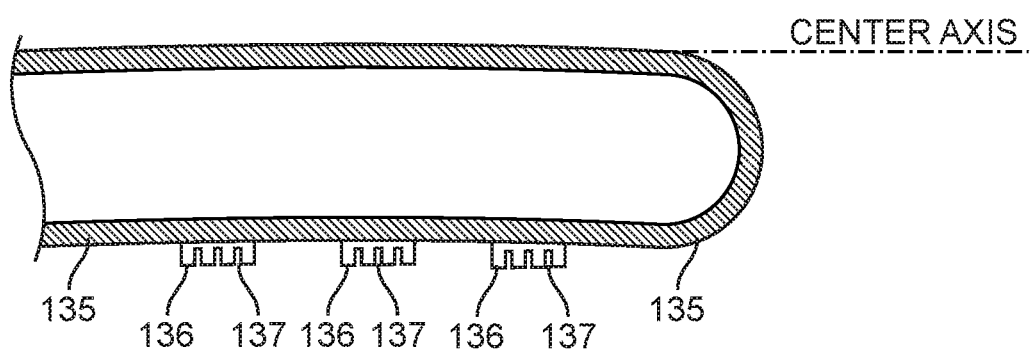
FIG. 14 illustrates in a cross-sectional view an everting balloon catheter with a material on the exterior surface of the everting membrane with multiple tissue collection areas by radial segments or stripes to biopsy different locations of a bodily passageway which may facilitate the extent or proliferation of a disease state.

FIG. 14 illustrates in a cross-sectional view an everting balloon catheter (not shown) with cellular collection materials 136 on multiple locations of the exterior surface of the everting membrane 135. Multiple tissue collection material 136 areas can be defined by radial segments or stripes to biopsy different locations of a bodily passageway which may facilitate or determine the extent or proliferation of a disease state within a bodily lumen. As an example, using the eversion process of everting membrane 135, assessing the cellular collection materials 136 in the more proximal portion of the device versus the more distal portion can provide the practitioner a rate of disease progression or treatment.

Figure 15A:
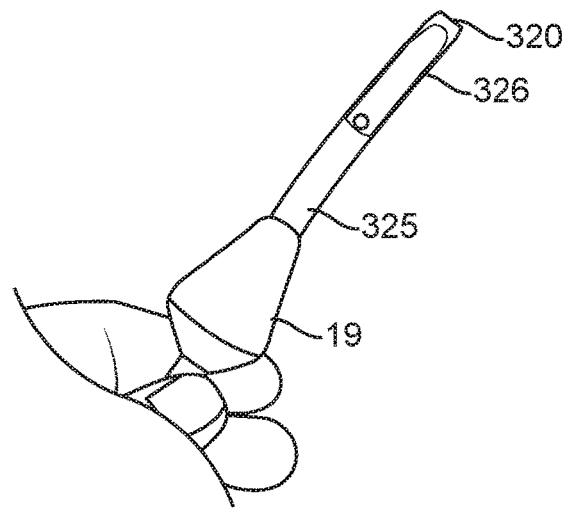
FIGS. 15A to 15E illustrate an everting balloon catheter with a material on the exterior surface of the everting membrane with multiple tissue collection areas placed on anterior and posterior locations of an everting membrane to define specific locations of studied cells or tissue in a body passageway.

FIGS. 15A to 15E illustrate an everting balloon catheter with a tissue collection material 326 on the exterior surface of the everting membrane 325 with multiple tissue collection material 326 areas placed on anterior and posterior locations of an everting membrane to assess specific locations of studied cells or tissue in a body passageway. FIG. 15A shows an initial stage of the eversion process with everting membrane 325 exiting the acorn tip 19 with the membrane rolling at a distal end 320 and tissue collection material 326 located within the everting membrane 325.

Figure 15B:
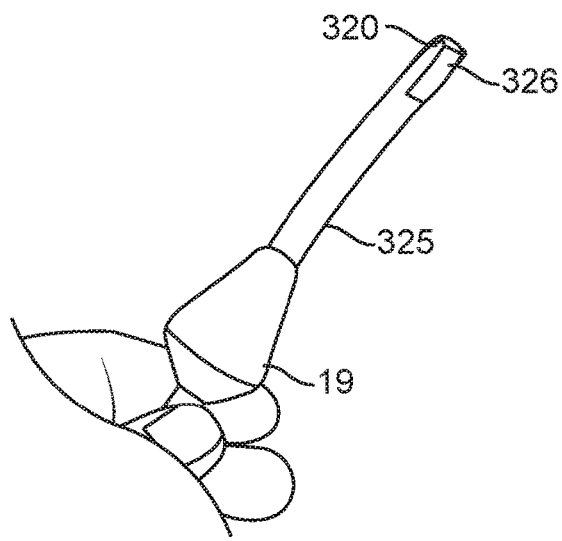

FIG. 15B demonstrates the eversion process proceeding with the everting membrane 325 having further exited the acorn tip 19 and tissue collecting material 326 rolling out of the distal end 320 of the everting membrane 325.

Figure 15C:
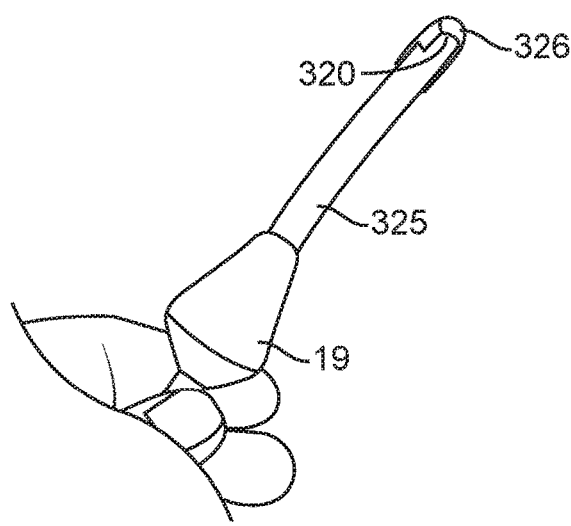

FIG. 15C further illustrates that the tissue collection material 326 is rolling out on two sides of the everting membrane 325 at the distal end 320.

Figure 15D:
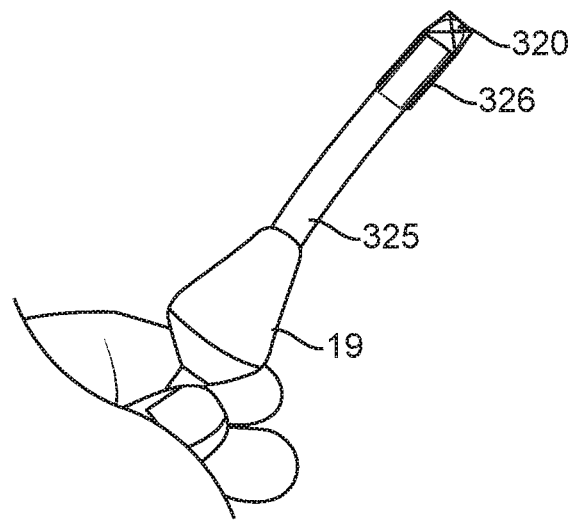

FIG. 15D illustrates the completion of the eversion process with the everting membrane 325 fully everted and tissue collection material 326 visible on one lateral side of everting membrane 325.

Figure 15E:
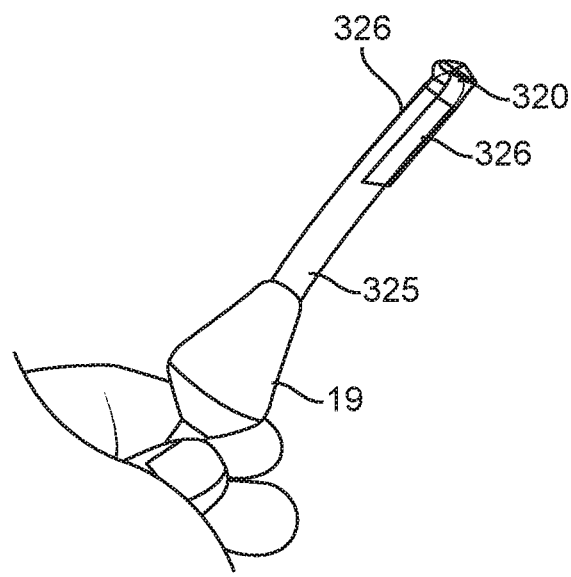

FIG. 15E shows tissue collection material 326 on both sides of everting membrane 325 to provide the ability to assess or diagnose two distinct areas, such as anterior portion and posterior portion, or lateral side and contralateral side, of a bodily lumen or passageway.

Figure 16A:
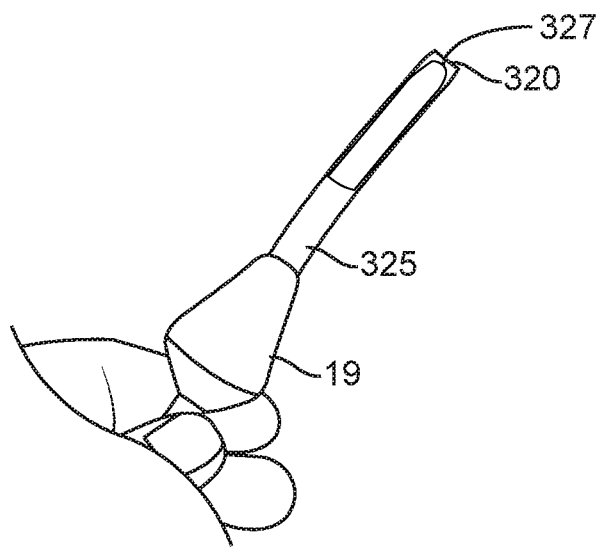
FIGS. 16A and 16D illustrate an everting balloon catheter with a material for collecting bodily fluid within a specific location in the body whereby the everting membrane lined on the exterior surface with a porous or fluid receptive membrane or material for fluid collection for bodily fluid collection at a specific bodily location within the passageway or body cavity.
Figure 16B:
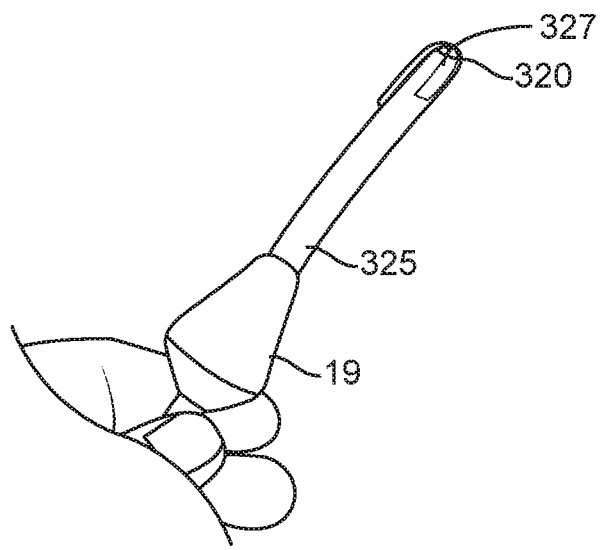
Figure 16C:
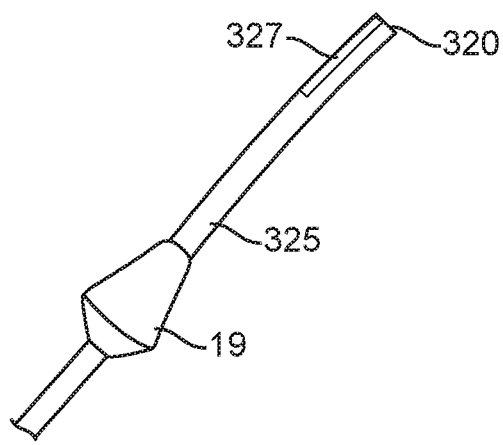
Figure 16D:
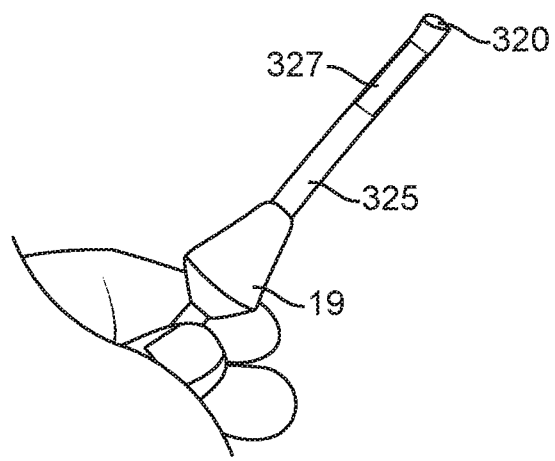

FIGS. 16A and 16D illustrate an everting balloon catheter with a material for collecting bodily fluid within a specific location in the body whereby the everting membrane lined on the exterior surface with a porous or fluid receptive membrane or material for fluid collection for bodily fluid collection at a specific bodily location within the passageway or body cavity. FIG. 16A shows the initial stages of the eversion process with everting membrane 325 exiting the distal end opening of acorn tip 19. Distal end 320 of everting membrane is visible and tissue collection material 327 is located and isolated within the everting membrane 325.

FIG. 16B shows a continuation of the eversion process with everting membrane 325 advanced further from acorn tip 19 and tissue collection material 327 just exiting the distal end 320 of the everting membrane 325.

FIG. 16C shows the completion of the eversion process with tissue collection material 327 located on one side of everting membrane 325 and just proximal to the distal end 320.

FIG. 16D shows the same tissue collection material 327 in another view located on one specific side of the everting membrane 325. Providing the tissue collection material 327 at a specific distance and specific location on everting membrane 325 provides the ability to directly diagnose a particular or specific area in a bodily passageway or lumen. Since the everting membrane 325 operates in the eversion process without shear forces, or without sliding along the interior surfaces of the body, tissue collection material 327 will be exposed within the body to only that tissue that contacts the material.

Figure 17A:
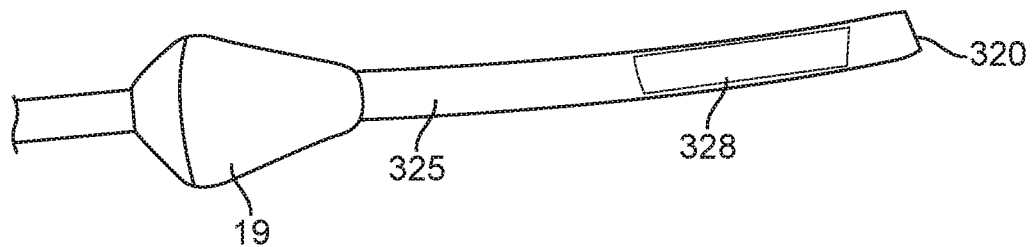
FIGS. 17A and 17B illustrate an everting balloon catheter with an everting balloon membrane with a diagnosing material on the external surface for determining pH, lactate, hormonal content, medication content, urine, fecal, blood, lymphatic fluid, bile, mucus, infection or pus, edema, or other detectable bodily fluid or by-product.
Figure 17B:
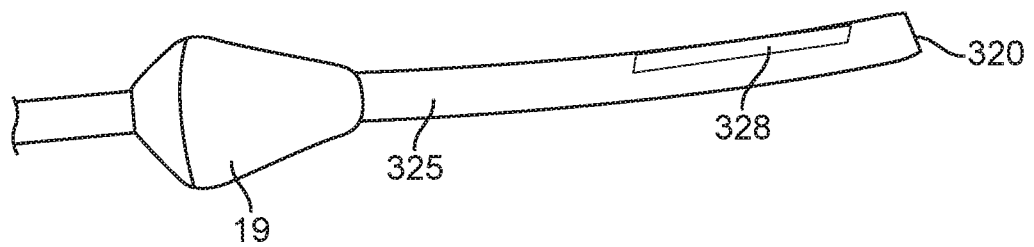

FIGS. 17A and 17B illustrate an everting balloon catheter with an everting balloon membrane 325 with a diagnosing material 328 on the external surface for determining pH, lactate, hormonal content, medication content, urine, fecal, blood, lymphatic fluid, bile, mucus, infection or pus, edema, or other detectable bodily fluid or by-product. Diagnosing material 328 is seen just proximal to the distal end 320 of the everting membrane 325 that is extended beyond the acorn tip 19. FIGS. 17A and 17B illustrate that the diagnosing material 328 located in a specific location on the everting membrane 325, but multiple diagnosing materials (not shown), or diagnosing materials that encompass the entire circumference or exterior surface of the everting membrane (not shown) are possible.

Figure 18:
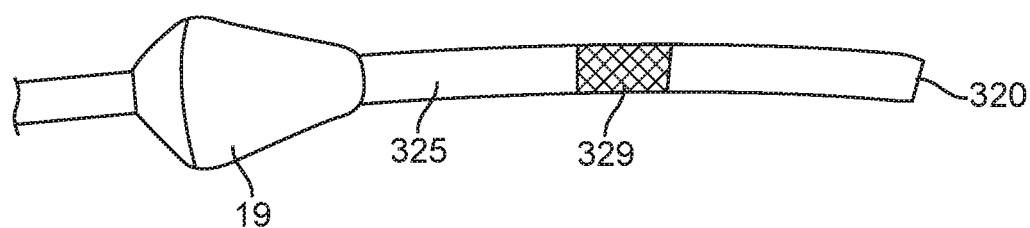
FIG. 18 illustrates an everting balloon catheter with an everting balloon membrane with a diagnosing material on the external surface that can detect and report temperature exposure, amount of pressure exerted as in pressure-sensitive test strips, or interior surface morphology of tissue within a bodily vessel.

In another embodiment, FIG. 18 illustrates an everting balloon catheter with an everting balloon membrane 325 with a diagnosing material 329 on the external surface of everting membrane 325 that can detect and report temperature exposure, amount of pressure exerted as in pressure-sensitive test strips, or interior surface morphology of tissue within a bodily vessel. As an example, pressure sensitive tape is used as diagnosing material 329 that is everted into a bodily passageway. Once everted, the hydraulic pressure within the everting catheter system can be increased to promote contact of the pressure sensitive tape to the tissue at a known pressure. The amount of internal hydraulic pressure can be reduced to then allow for inversion and removal from the body of the patient. After removal, the pressure sensitive tape or diagnosing material can be evaluated. Other types of evaluation include internal tissue morphology or temperature.

Figure 19:
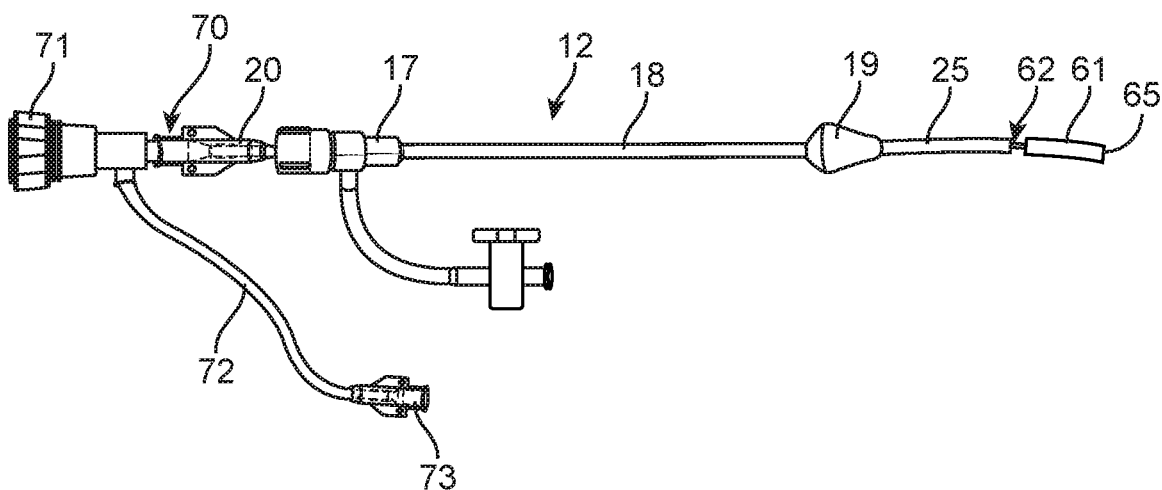
FIG. 19 illustrates a biopsy everting catheter system that includes a through-lumen within the inner catheter for irrigation or lavage of tissue to facilitate cellular or specimen collection.

FIG. 19 illustrates a biopsy everting catheter system 12 that includes a through-lumen within the inner catheter (not visible) for irrigation or lavage of tissue through port 73 and tubing 72. Lavage or fluid exits everting membrane 25 at the distal end 62 near biopsy device 61 (illustrated here with a cytology brush but other biopsy instruments are possible) to facilitate cellular or specimen collection.

Figure 20:
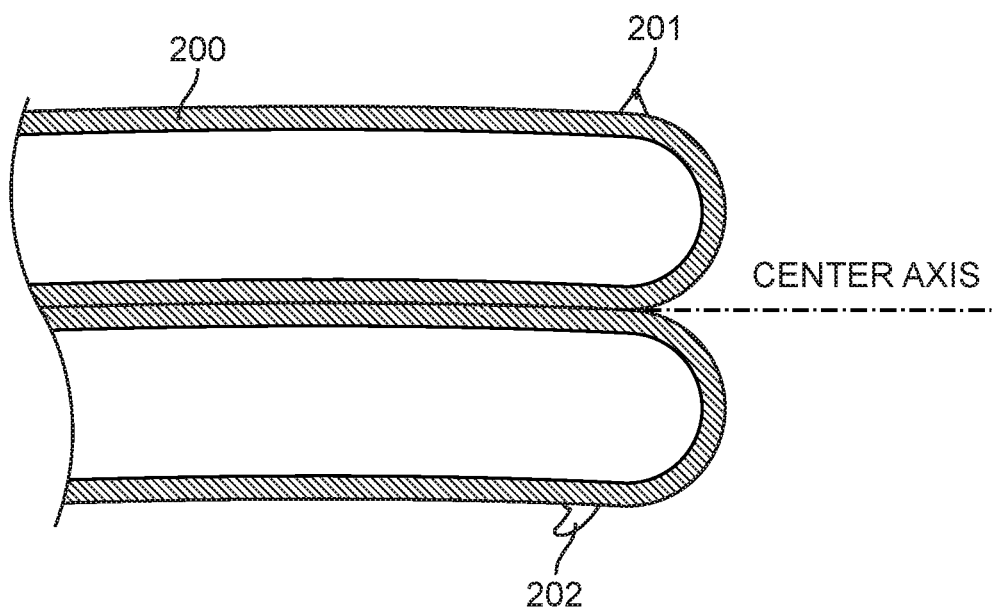
FIG. 20 illustrates in a cross-sectional view a biopsy everting catheter system with a tissue agitator on the everting membrane to facilitate tissue or cellular collection.
Figure 21:
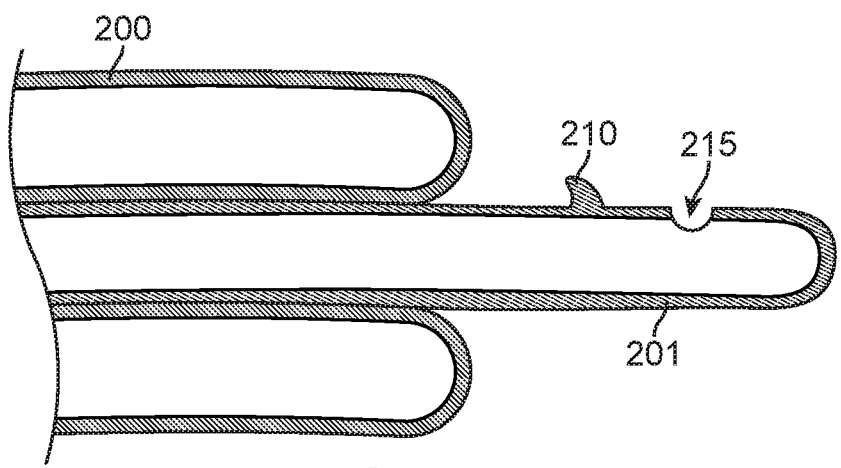
FIG. 21 illustrates a biopsy everting catheter system with a tissue agitator on the inner catheter of the biopsy device that performs the function of agitation automatically upon eversion or inversion.

FIG. 20 illustrates in a cross-sectional view a biopsy everting catheter system with tissue agitators 201 and 202 on the everting membrane 200 to facilitate tissue or cellular collection. Tissue agitators 201 and 202 are exposed to the tissue once everted from everting membrane 200. Tissue agitators 201 and 202 can also be used in conjunction with physically advancing, retracting, or rotating the entire everting catheter system FIG. 21 illustrates a biopsy everting catheter system with a tissue agitator 210 on the inner catheter of the biopsy device 201 that performs the function of agitation automatically upon eversion or inversion. Tissue agitator 210 is designed to loosen or disrupt tissue to facilitate collection in side hole opening 215 of biopsy device 201.

Figure 22:
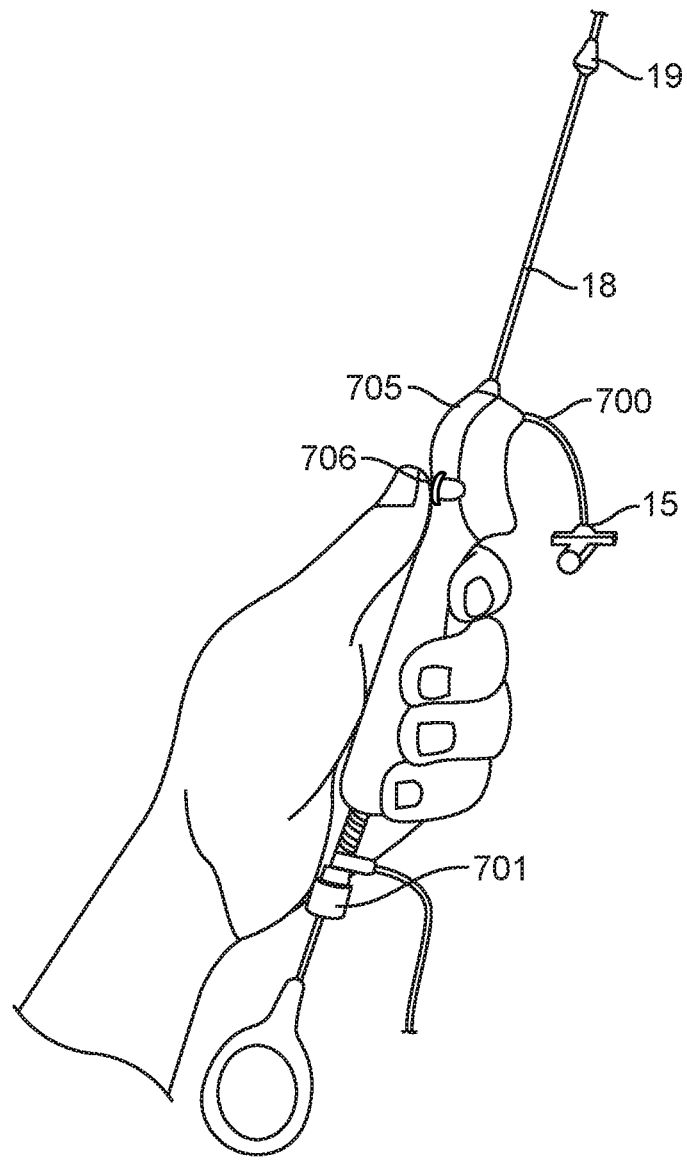
FIG. 22 illustrates a biopsy everting catheter system with a handle for the manual advancement or retraction, or rotation, the entire everting catheter system to facilitate tissue agitation to increase the amount of tissue for specimen collection.

FIG. 22 illustrates a biopsy everting catheter system 700 with handle 705 for the manual advancement, retraction, or rotation, of the entire everting catheter system to facilitate tissue agitation to increase the amount of tissue for specimen collection. Handle button 706 can be used by the physician or operator to physically evert or invert the everting membrane (not visible in outer catheter 18). Or handle button can be connected to biopsy device 701 for the one handed manual advancement, retraction, or rotation of the biopsy device.

Figure 23A:
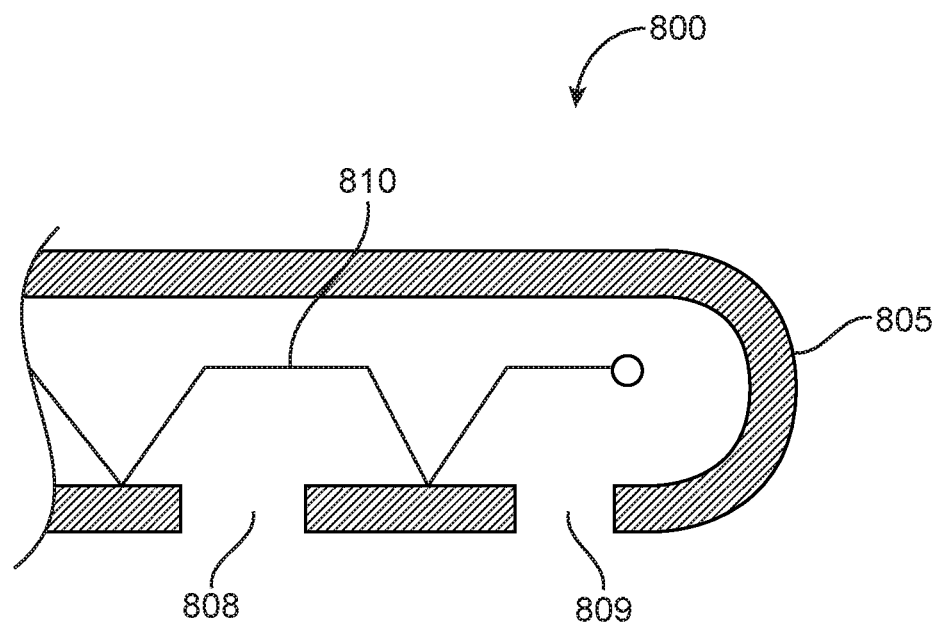
FIGS. 23A to 23C illustrate a tissue shaver for removing and collecting thin layers of tissue within the uterine cavity that can be used for atrophic endometrium or post-menopausal women.
Figure 23B:
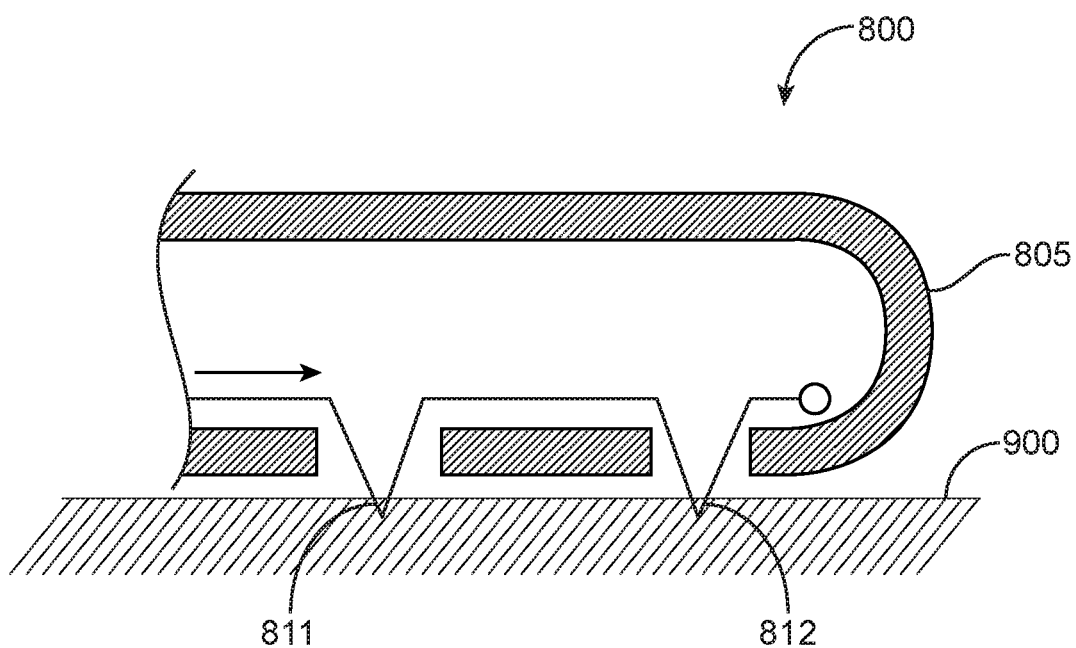
Figure 23C:
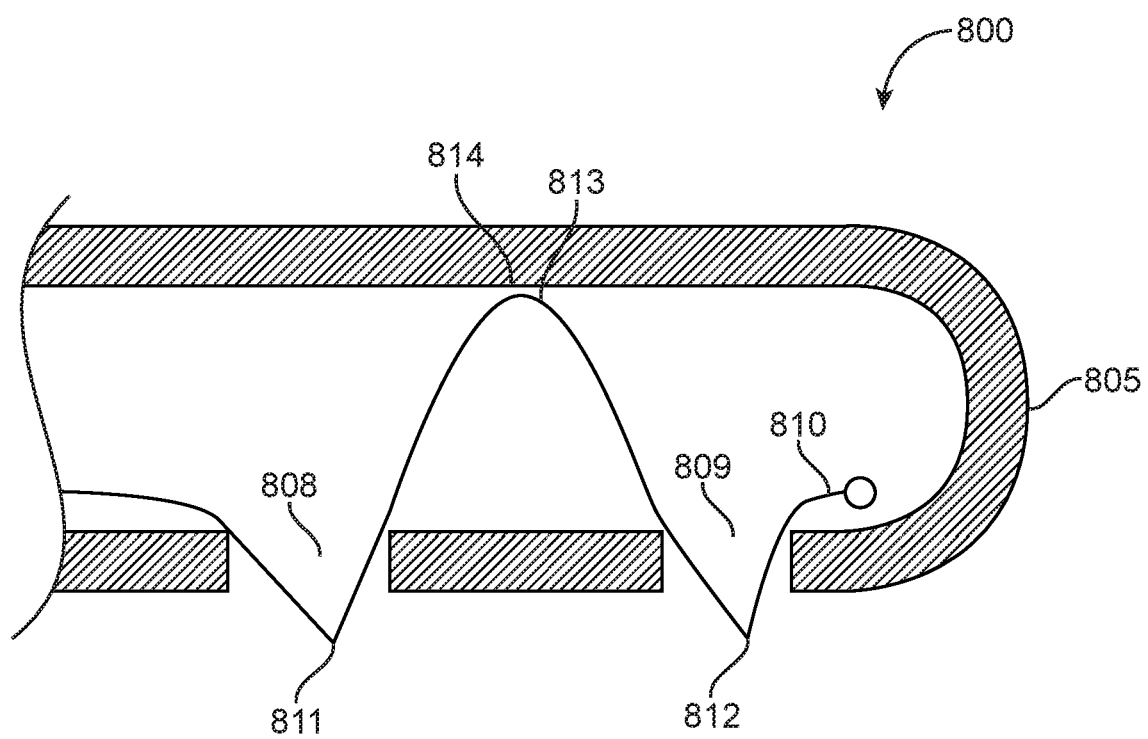

FIGS. 23A-23C illustrate in cross-section a tissue shaver 800 for removing and collecting thin layers of tissue within the uterine cavity that is particularly suited for atrophic endometrium or post-menopausal women. Tissue shaver 800 has a distal catheter 805 that can have side holes 808 and 809 with internal nitinol wire 810 within the lumen of distal catheter 805.

FIG. 23A illustrates a variation of the configuration of the internal nitinol wire 810 as the tissue shaver 800 can be placed within the uterine cavity or bodily lumen. FIG. 23B illustrates that once placed within the uterine cavity or other bodily lumen, the internal nitinol wire 810 can be advanced within the lumen of distal catheter 805. Upon advancement, nitinol wire projections 811 and 812 can exit side holes 808 and 809 for exposure within endometrium 900 or other tissue as defined by the bodily lumen. Nitinol wire projection 811 and 812 can be configured to cut or shave tissue when the distal catheter 805 is rotated within the tissue or endometrium 900.

FIGS. 23A and 23B illustrate a distal catheter 805 with two side holes 808 and 809 but a singular side hole, as well as a higher number of side holes is possible. The side holes can be configured diametrically opposite to each other or co-linear on the surface of distal catheter 805 as shown in FIGS. 23A and 23B. In operation, the distal catheter 805 can exit an everting membrane (not shown) or be placed within the patient as a single cannula catheter.

FIG. 23C illustrates the biasing force 813 on the internal nitinol wire 810 that can force nitinol wire projections 811 and 812 to exit side holes 808 and 809. Biasing force 813 can act upon inner lumen surface 814 to force nitinol wire projections 811 and 812 out of side holes 808 and 809 when the internal nitinol wire 810 is advanced within the lumen of the distal catheter 805.

Figure 24:
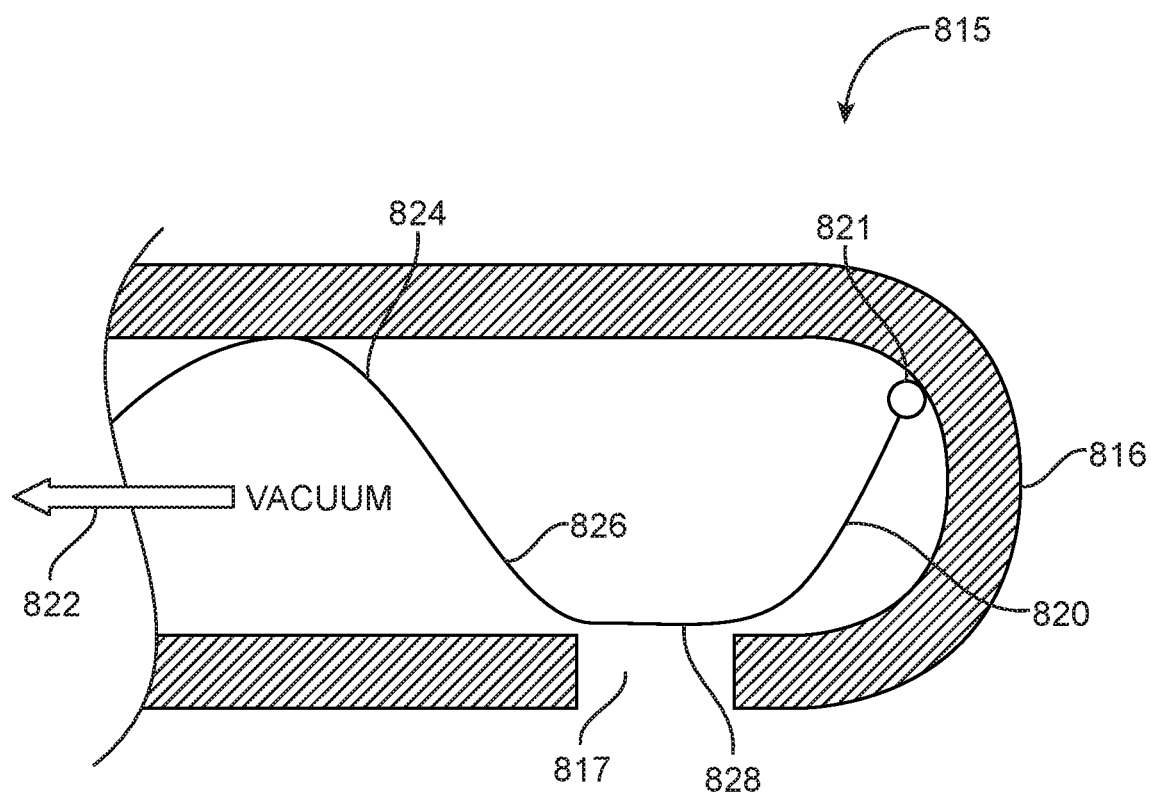
FIG. 24 illustrates in cross section a tissue shaver with internal cutting apparatus with internal aspiration.

FIG. 24 illustrates in cross section a tissue shaver 815 with internal cutting wire 820 that can be housed within the lumen of a distal catheter 816. The lumen of the distal catheter 816 can be coupled with an internal aspiration source (not shown) that supplies vacuum pressure 822 that force endometrium or bodily lumen tissue (not shown) within side hole 817. Cutting wire 820 can be coupled to an actuator or motor on the proximal portion of the catheter (not shown) that rotates cutting wire 820 within the lumen of distal catheter 816. Distal end of cutting wire 820 is shown with distal cutting wire ball tip 821 that can facilitate the movement of cutting wire 820 within the lumen of distal catheter 816. In operation, once deployed in the uterine cavity or bodily lumen, suction or vacuum force 822 can be applied to force endometrium and bodily lumen tissue within side hole 817. In combination, the rotation of cutting wire 820 can slice tissue that protrudes inside side hole 817. Cutting wire 820 can be configured with a biasing force 824 and wire curvature 826 to force the cutting portion 828 to slice tissue at side hole 817. Alternatively, tissue shaver 815 can be used without a vacuum force 822 or internal aspiration source.

FIG. 24 illustrates one side hole 817 but multiple side holes at different locations on the distal catheter 816 are possible. Cutting wire 820 can be configured as a coil or spring (not shown). The coil or spring can be made from round wire, flat wire, D-shaped wire, or a wire surface with multiple facets. As a coil or spring, this cutting wire mechanism can be rotated within the lumen of a distal catheter, or separately or in combination, advanced and retracted to provide a cutting surface at the side hole of a distal catheter. This cutting action can be performed with or without a vacuum force.

Figure 25:
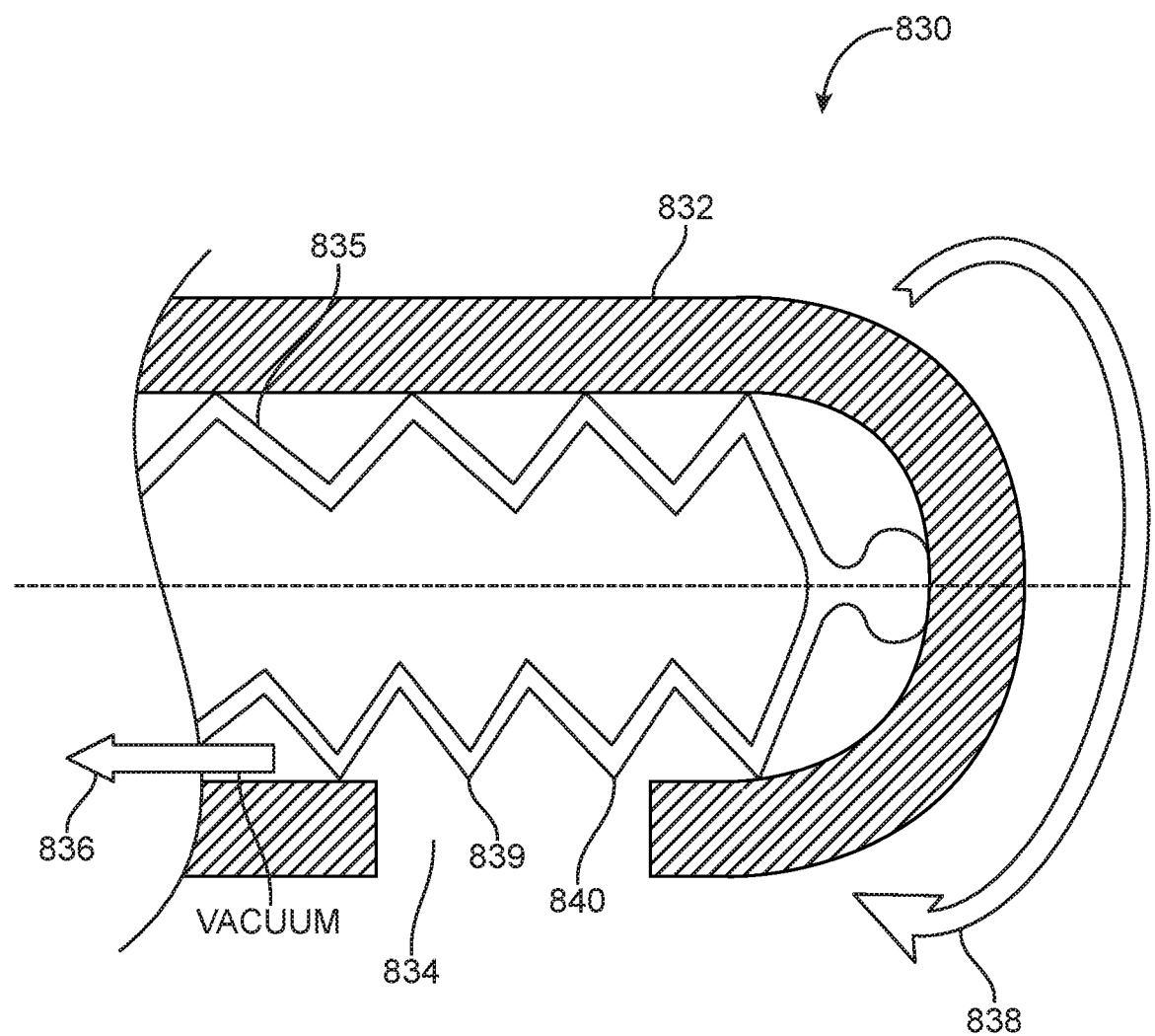
FIG. 25 illustrates a tissue shaver that can include an internal coring apparatus.

FIG. 25 illustrates in cross section a tissue shaver 830 that can include an internal coring screw 835 within distal catheter 832 with side hole 834. Lumen of distal catheter 832 can be coupled to an aspiration source (not shown) that supplies vacuum force 836. In operation when distal catheter 832 is placed within the uterine cavity or bodily lumen, vacuum force 836 can be applied to force endometrium or bodily lumen tissue within side hole 834. Optionally in combination, actuator or motor (not shown) at the proximal portion of the tissue shaver 830 can be coupled to the internal coring screw 835 to provide rotation 838 to the internal coring screw 835, which can rotate with or independently of the distal catheter 832. Internal coring screw 835 can contain a pitch in which screw threads 839 and 840 remove endometrium and bodily lumen tissue as the internal coring screw 835 is rotated. Endometrium and bodily lumen tissue as it is removed at side hole 834 can be driven towards the proximal portion of distal catheter 832 in combination with the rotation of the internal coring screw 835 and vacuum force 836 to a specimen collection area (not shown) in the proximal portion of tissue shaver 830. Internal coring screw 835 and tissue shaver 830 can be used without a coupled aspiration source. Distal catheter 832 can have a plurality of side holes in various locations on the distal catheter. For specimen collection, after removal from the uterine cavity or bodily lumen, the actuator or motor can be applied in the opposite direction to push endometrium and bodily lumen tissue back towards side hole 834 for removal from the distal catheter 830.

Figure 26A:
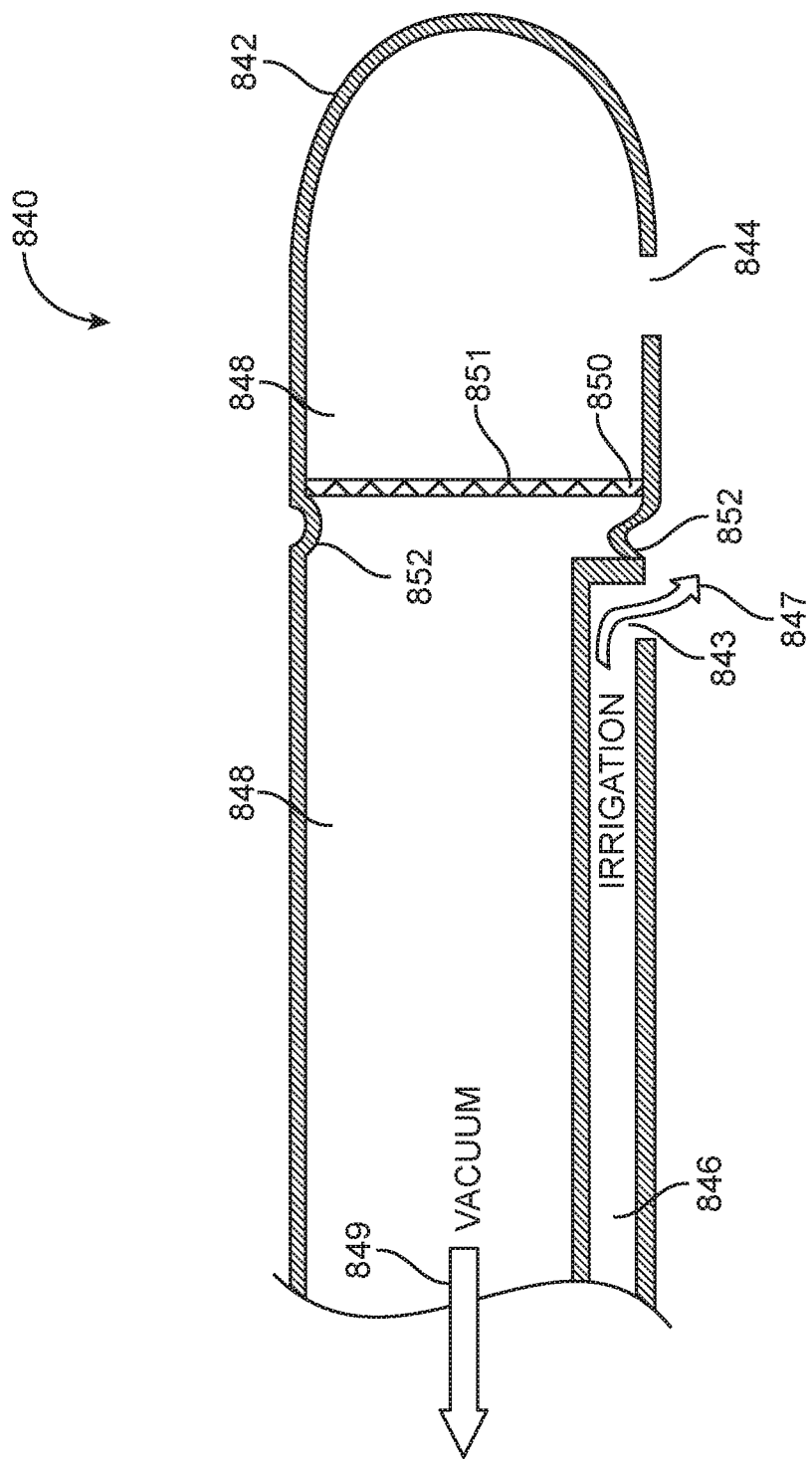
FIGS. 26A and 26B illustrate in cross section a tissue collector that can include a mechanism for cellular collection and sampling.
Figure 26B:
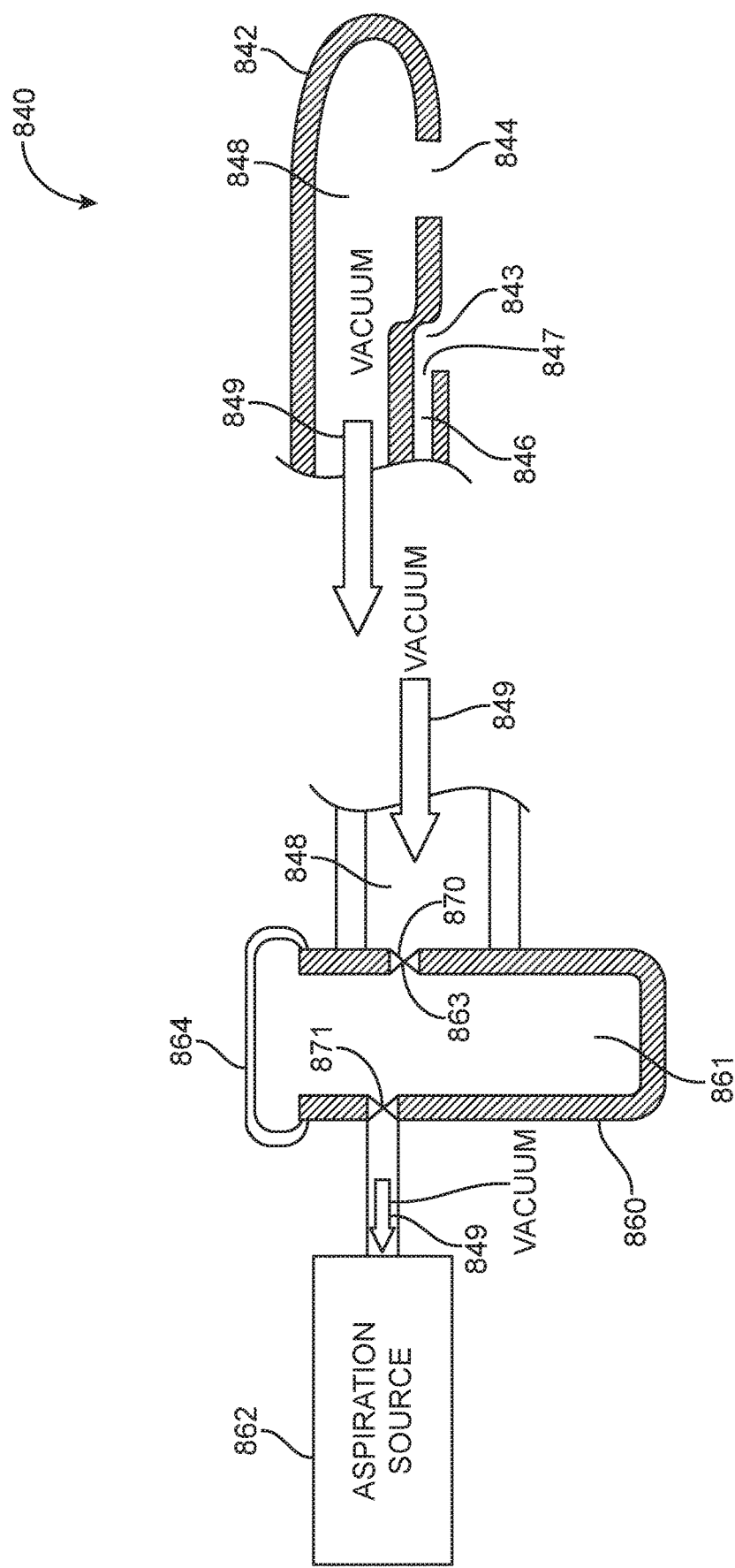

FIGS. 26A and 26B illustrate in cross section tissue collector 840 with distal catheter 842 with irrigation lumen 846 that can be coupled to an irrigation source (not shown) operated by the user or physician that provides irrigation 847 through irrigation side hole 843. Fluid media for irrigation 847 can include saline or culture media depending upon the application. Distal catheter 842 can have aspiration side hole 844 that can be coupled to aspiration lumen 848. An aspiration source (not shown) at the proximal portion of the tissue collector can provide vacuum force 849. Proximal to the aspiration side hole 844, filtration membrane 850 can have a porosity for collecting certain sized cells or tissue. Filtration membranes can include a 0.2 micron to 15 micron filter, or other porosities, for example to drive a vacuum or pressure differential across filtration membrane 850 but leaving cellular or tissue contents on the distal side 851 of the filtration membrane. In operation once the distal catheter 842 is placed within the uterine cavity or bodily lumen, media 847 can be introduced through irrigation lumen 846 and out into the patient through irrigation side hole 843. Vacuum force 849 can be applied within aspiration lumen 848 to drive contents from the uterine cavity or bodily lumen into aspiration side hole 844. Filtration membrane 850 can trap tissue or cellular contents on the distal side 851 of the filtration membrane 850. Distal catheter 842 can then be removed from the patient. To obtain the tissue or cellular specimen, distal catheter 842 can be configured with a perforation or preferential weakness 852 that allows the end user to snap off the filtration membrane 850 from distal catheter 842 for subsequent analysis of the collected tissue or cellular contents. Aspiration side hole 844 can be used a portal to retrieve collected tissue. Tissue collector 840 can be used without irrigation lumen 846 and irrigation media 847. Multiple irrigation side holes could be employed. Multiple aspiration side holes could be used, or combinations and numbers of irrigation and aspirations side holes. Multiple filtration membranes could be employed in which different porosities are used. For example, the most distal or first filtration membrane can have a larger porosity with a second, more proximal filtration membrane having a smaller or finer porosity to collect a specific size of tissue or cells that would flow through the first filtration membrane. A portal can be between the first and second membranes, for example to retrieve collected tissue or cells between the two filtration membranes. A perforation or preferential weakness in the distal catheter can, for example, retrieve tissue or cells between the two filtration membranes. A plurality of filtration membranes can be used.

FIG. 26B illustrates in cross section a tissue collector 840 with tissue or cellular collection area 860 in the proximal portion of the tissue collector. Aspiration source 862 can provide vacuum force 849 through the tissue or cellular collection area 860 through filtration membranes 871 and 870, and ultimately through the aspiration lumen 848 to the distal catheter 842 and aspiration side hole 844. Tissue or cellular collection area 860 can be removed by the user following the sampling procedure in which cap 864 can be removed to access the specimen in collection area 861. Irrigation lumen 846 can provide media 847 through irrigation side hole 843 and filtration system that includes an irrigation source for the uterine cavity. As described in FIG. 26A, the tissue collector 840 illustrated in FIG. 26B could be used without irrigation lumen 846 and irrigation media 847. Multiple irrigation side holes could be employed. Multiple aspiration side holes can be used, or combinations and numbers of irrigation and aspirations side holes.

Any of the apparatus and/or method elements described herein can be used in combination with or substituted with any of the apparatus and/or method elements of U.S. Provisional Application Nos. 61/302,742, filed Nov. 11, 2013; 61/977,478, filed Apr. 9, 2014; 62/005,355, filed May 30, 2014; 62/528,422, filed Jul. 3, 2017; 62/553,057, filed Aug. 31, 2017; 62/007,339, filed Jun. 3, 2014; and 62/597,353, filed Dec. 11, 2017, all of which are incorporated by reference herein in their entireties.

Any elements described herein as singular can be pluralized (i.e., anything described as "one" can be more than one). Any species element of a genus element can have the characteristics or elements of any other species element of that genus. The media delivered herein can be any of the fluids (e.g., liquid, gas, or combinations thereof) described herein. The patents and patent applications cited herein are all incorporated by reference herein in their entireties. Some elements may be absent from individual figures for reasons of illustrative clarity. The above-described configurations, elements or complete assemblies and methods and their elements for carrying out the disclosure, and variations of aspects of the disclosure can be combined and modified with each other in any combination. All devices, apparatuses, systems, and methods described herein can be used for medical (e.g., diagnostic, therapeutic or rehabilitative) or non-medical purposes.

We claim:

1. A method for retrieving a tissue sample from a uterus comprising:
    inserting a distal end of an elongated element into the uterus, wherein the elongated element has a lateral opening and a cover closeable over the lateral opening;
    positioning the tissue sample in the elongated element; and
    everting the cover over the opening.

2. The method of claim 1, further comprising lavaging of the uterus with at least an irrigation fluid through the lateral opening.

3. The method of claim 2, wherein the positioning comprises aspirating of the tissue and irrigation fluid through the lateral opening.

4. The method of claim 2, wherein the lavaging comprises cellular collection.

5. The method of claim 2, wherein the lavaging comprises specimen collection.

6. The method of claim 2, further comprising delivery of a cytology element into the uterus.

7. The method of claim 2, further comprising delivery of a biopsy element into the uterus.

8. The method of claim 2, wherein the elongated element has an inner catheter, and wherein the inner catheter has a through-lumen, and wherein the method comprises delivering irrigation fluid through the through-lumen.

9. The method of claim 1, further comprising delivering contrast media or echogenic fluid through the lateral opening.

10. The method of claim 1, further comprising aspirating contrast media or echogenic fluid through the lateral opening.

11. The method of claim 1, further comprising delivering medication through the lateral opening.

12. The method of claim 1, further comprising delivering therapeutic fluid through the lateral opening.

13. The method of claim 1, further comprising aspirating medication through the lateral opening.

14. The method of claim 2, further comprising delivery of a lavage fluid exiting through the cover.

15. The method of claim 1, further comprising lavaging of the uterus.

16. The method of claim 15, wherein the positioning comprises aspirating of the tissue.

17. The method of claim 15, wherein the lavaging comprises cellular collection.

18. The method of claim 15, wherein the lavaging comprises specimen collection.

19. The method of claim 15, further comprising delivery of a cytology element into the uterus.

20. The method of claim 15, further comprising delivery of a biopsy element into the uterus.

* * * * *